(12) United States Patent
Benner et al.

(10) Patent No.: US 7,786,084 B2
(45) Date of Patent: Aug. 31, 2010

(54) TREATMENT OF BURNS

(75) Inventors: Robbert Benner, Barendrecht (NL); Nisar A. Khan, Rotterdam (NL)

(73) Assignee: Biotempt B.V., Koekange (NL)

( * ) Notice: Subject to any disclaimer, the term of this patent is extended or adjusted under 35 U.S.C. 154(b) by 33 days.

(21) Appl. No.: 11/981,505

(22) Filed: Oct. 30, 2007

(65) Prior Publication Data

US 2008/0171094 A1 Jul. 17, 2008

Related U.S. Application Data

(63) Continuation-in-part of application No. 10/409,694, filed on Apr. 8, 2003, now abandoned, which is a continuation-in-part of application No. 10/028,075, filed on Dec. 21, 2001, now abandoned.

(51) Int. Cl.
A61K 38/06 (2006.01)
A61K 38/07 (2006.01)
A61K 38/08 (2006.01)

(52) U.S. Cl. ................................ 514/16; 514/17; 514/18

(58) Field of Classification Search ........................ None
See application file for complete search history.

(56) References Cited

U.S. PATENT DOCUMENTS

| | | | |
|---|---|---|---|
| 4,330,466 A | 5/1982 | Yanaihara et al. |
| 4,427,660 A | 1/1984 | Schiffman et al. |
| 4,571,336 A | 2/1986 | Houck et al. |
| 4,753,965 A | 6/1988 | Stemerick et al. |
| 4,855,285 A | 8/1989 | Stevens |
| 4,966,848 A | 10/1990 | Smith et al. |
| 4,977,244 A | 12/1990 | Muchmore et al. |
| 5,002,961 A | 3/1991 | Dage et al. |
| 5,010,175 A | 4/1991 | Rutter et al. |
| 5,055,447 A | 10/1991 | Palladino et al. |
| 5,102,393 A | 4/1992 | Sarnoff et al. |
| 5,223,397 A | 6/1993 | Pouletty |
| 5,223,421 A | 6/1993 | Smith et al. |
| 5,308,834 A | 5/1994 | Scott et al. |
| 5,380,668 A | 1/1995 | Herron |
| 5,436,270 A | 7/1995 | Wang |
| 5,677,275 A | 10/1997 | Lunardi-Iskandar et al. |
| 5,700,781 A | 12/1997 | Harris |
| 5,801,193 A | 9/1998 | Ojo-Amaize et al. |
| 5,837,218 A | 11/1998 | Peers et al. |
| 5,837,478 A | 11/1998 | Gallatin et al. |
| 5,851,997 A | 12/1998 | Harris |
| 5,854,004 A | 12/1998 | Czemilofsky et al. |
| 5,856,440 A | 1/1999 | Wang |
| 5,877,148 A | 3/1999 | Lunardi-Iskandar et al. |
| 5,942,494 A | 8/1999 | Ginsberg et al. |
| 5,958,413 A | 9/1999 | Anagnostopulos et al. |
| 5,966,712 A | 10/1999 | Sabatini et al. |
| 5,968,513 A | 10/1999 | Gallo et al. |
| 5,972,924 A | 10/1999 | Keep et al. |
| 5,981,486 A | 11/1999 | Matsushima et al. |
| 5,994,126 A | 11/1999 | Steinman et al. |
| 5,997,871 A | 12/1999 | Gallo et al. |
| 6,022,696 A | 2/2000 | Harding et al. |
| 6,051,596 A | 4/2000 | Badger |
| 6,075,150 A | 6/2000 | Wang et al. |
| 6,086,918 A | 7/2000 | Stern et al. |
| 6,150,500 A | 11/2000 | Salerno |
| 6,207,145 B1 | 3/2001 | Tovey |
| 6,235,281 B1 | 5/2001 | Stenzel et al. |
| 6,271,199 B2 | 8/2001 | Brand et al. |
| 6,278,794 B1 | 8/2001 | Parekh et al. |
| 6,309,822 B1 | 10/2001 | Fodor et al. |
| 6,310,041 B1 | 10/2001 | Haddox et al. |
| 6,319,504 B1 | 11/2001 | Gallo et al. |
| 6,329,573 B1 | 12/2001 | Lightfoot et al. |
| 6,361,992 B1 | 3/2002 | Szkudlinski et al. |
| 6,379,970 B1 | 4/2002 | Liebler et al. |
| 6,416,959 B1 | 7/2002 | Giuliano et al. |
| 6,489,296 B1 | 12/2002 | Grinnell et al. |
| 6,507,788 B1 | 1/2003 | Camara y Ferrer et al. |
| 6,518,021 B1 | 2/2003 | Thastrup et al. |
| 6,539,102 B1 | 3/2003 | Anderson et al. |
| 6,583,109 B1 | 6/2003 | Gallo et al. |
| 6,586,403 B1 | 7/2003 | Mathison et al. |
| 6,596,688 B1 | 7/2003 | Gallo et al. |
| 6,620,416 B1 | 9/2003 | Gallo et al. |
| 6,630,138 B2 | 10/2003 | Gerlitz et al. |
| 6,642,201 B1 | 11/2003 | Khavinson et al. |
| 6,645,934 B1 | 11/2003 | Rodemann et al. |
| 6,652,860 B1 | 11/2003 | Singh et al. |
| 6,699,656 B2 | 3/2004 | Gallo et al. |

(Continued)

FOREIGN PATENT DOCUMENTS

DE 19953339 5/2001

(Continued)

OTHER PUBLICATIONS

Abeyama et al., A role of NF-κB-dependent gene transactivation in sunburn. The Journal of Clinical Investigation, vol. 105, No. 12, pp. 1751-1759, Jun. 2000.

(Continued)

Primary Examiner—Jeffrey E Russel
(74) Attorney, Agent, or Firm—TraskBritt

(57) ABSTRACT

The invention relates to the treatment of burn injuries. Described are methods for modulating a burn injury in a subject, the method comprising providing the subject with a gene-regulatory peptide or functional analogue thereof, e.g., LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LPGC (SEQ ID NO:19), MTRV (SEQ ID NO:20), MTR, and VVC. Also described is the use of an NF-kappaB down-regulating peptide or functional analogue thereof for the production of a pharmaceutical composition for the treatment of burn injury of a subject.

8 Claims, 12 Drawing Sheets

U.S. PATENT DOCUMENTS

| | | | |
|---|---|---|---|
| 6,711,563 B1 | 3/2004 | Koskas | |
| 6,727,227 B1 | 4/2004 | Khavinson | |
| 6,783,757 B2 | 8/2004 | Brudnak | |
| 6,831,057 B2 | 12/2004 | Baldwin et al. | |
| 6,844,315 B2 | 1/2005 | Khan et al. | |
| 6,852,697 B1 | 2/2005 | Mathison et al. | |
| 6,894,028 B2 | 5/2005 | Lipton et al. | |
| 6,921,751 B1 | 7/2005 | Khan et al. | |
| 7,094,760 B2 | 8/2006 | Mathison et al. | |
| 7,135,286 B2 | 11/2006 | Margus et al. | |
| 7,175,679 B2 | 2/2007 | Khan et al. | |
| 7,316,819 B2 | 1/2008 | Crotts et al. | |
| 7,358,330 B2 | 4/2008 | Khan et al. | |
| 7,365,155 B2 | 4/2008 | Khan et al. | |
| 7,368,535 B2 | 5/2008 | Gorczynski et al. | |
| 7,402,322 B2 | 7/2008 | Khan et al. | |
| 7,501,391 B2 | 3/2009 | Khan et al. | |
| 7,517,529 B2 | 4/2009 | Khan et al. | |
| 7,524,820 B1 | 4/2009 | Khan et al. | |
| 7,560,433 B2 | 7/2009 | Khan et al. | |
| 7,576,174 B2 | 8/2009 | Benner et al. | |
| 2002/0041871 A1 | 4/2002 | Brudnak | |
| 2002/0064501 A1 | 5/2002 | Khan et al. | |
| 2002/0147306 A1 | 10/2002 | Lin et al. | |
| 2003/0049273 A1 | 3/2003 | Gallo et al. | |
| 2003/0113733 A1 | 6/2003 | Khan et al. | |
| 2003/0119720 A1 | 6/2003 | Khan et al. | |
| 2003/0166556 A1 | 9/2003 | Khan et al. | |
| 2003/0186244 A1 | 10/2003 | Margus et al. | |
| 2003/0215434 A1 | 11/2003 | Khan et al. | |
| 2003/0219425 A1 | 11/2003 | Khan et al. | |
| 2003/0220257 A1 | 11/2003 | Benner et al. | |
| 2003/0220258 A1 | 11/2003 | Benner et al. | |
| 2003/0220259 A1 | 11/2003 | Benner et al. | |
| 2003/0220260 A1* | 11/2003 | Khan et al. | 514/12 |
| 2003/0220261 A1 | 11/2003 | Khan et al. | |
| 2003/0224995 A1 | 12/2003 | Khan et al. | |
| 2004/0013661 A1 | 1/2004 | Wensvoort et al. | |
| 2004/0208885 A1* | 10/2004 | Khan et al. | 424/185.1 |
| 2005/0037430 A1 | 2/2005 | Khan et al. | |
| 2005/0107314 A1 | 5/2005 | Gorczynski et al. | |
| 2005/0214943 A1 | 9/2005 | Khan et al. | |
| 2005/0227925 A1 | 10/2005 | Benner et al. | |
| 2006/0111292 A1 | 5/2006 | Khan et al. | |
| 2006/0142205 A1 | 6/2006 | Benner et al. | |
| 2006/0173162 A1 | 8/2006 | Djurup et al. | |
| 2006/0275255 A1 | 12/2006 | Gudkov | |
| 2007/0111948 A1 | 5/2007 | Turdiev | |
| 2007/0197447 A1 | 8/2007 | Khan et al. | |
| 2008/0076714 A1 | 3/2008 | Khan et al. | |
| 2008/0171094 A1 | 7/2008 | Benner et al. | |
| 2008/0176243 A1 | 7/2008 | Khan et al. | |
| 2008/0194489 A1 | 8/2008 | Khan et al. | |
| 2008/0242618 A1 | 10/2008 | Khan et al. | |
| 2008/0242837 A1 | 10/2008 | Khan et al. | |

FOREIGN PATENT DOCUMENTS

| | | |
|---|---|---|
| EP | 0 572 688 | 5/1997 |
| EP | 1 138 692 A1 | 10/2001 |
| EP | 1 300 418 | 4/2003 |
| EP | 1 224 212 B1 | 7/2003 |
| EP | 1 466 612 A1 | 10/2004 |
| GB | 2 194 886 A | 3/1988 |
| JP | 09-176187 A | 7/1997 |
| WO | WO 92/20795 A1 | 11/1992 |
| WO | WO 96/04008 | 2/1996 |
| WO | WO 96/33218 | 10/1996 |
| WO | WO 97/49373 | 12/1997 |
| WO | WO 97/49418 | 12/1997 |
| WO | WO 97/49432 | 12/1997 |
| WO | WO 97/49721 | 12/1997 |
| WO | WO 98/06742 | 2/1998 |
| WO | WO 98/34631 A1 | 8/1998 |
| WO | WO 98/35691 | 8/1998 |
| WO | WO 99/31227 | 6/1999 |
| WO | WO 99/59617 | 11/1999 |
| WO | WO 00/17348 | 3/2000 |
| WO | WO 01/10907 A2 | 2/2001 |
| WO | WO 01/11048 A2 | 2/2001 |
| WO | WO 0110457 A2 | 2/2001 |
| WO | WO 01/29067 | 4/2001 |
| WO | WO 01/29069 A1 | 4/2001 |
| WO | WO 01/32196 A1 | 5/2001 |
| WO | WO 01/36454 A1 | 5/2001 |
| WO | WO 01/51508 A1 | 7/2001 |
| WO | WO 01/68113 A1 | 9/2001 |
| WO | WO 01/72831 | 10/2001 |
| WO | WO 01/83554 A2 | 11/2001 |
| WO | WO 02/085117 | 10/2002 |
| WO | WO 03/029292 A2 | 4/2003 |
| WO | WO 2006/069198 A1 | 6/2006 |

OTHER PUBLICATIONS

Abraham, E., "Coagulation Abnormalities in Acute Lung Injury and Sepsis," Am. J. Respir. Cell Mol. Biol., 2000, pp. 401-404, vol. 22.

Adib-Conquy et al., "NF-κB Expression in Mononuclear Cells in Patients with Sepsis Resembles That Observed in Lipopolysaccharide Tolerance," Am. J. Respir. Crit. Care Med., 2000, pp. 1877-1883, vol. 162.

Agawal et al., Acute Renal Failure, American Family Physician, 2000, pp. 2077-2088, vol. 61, corresponding to web version of p. 1-12.

Albini et al., "Old drugs as novel angiogenesis inhibitors: Preclinical studies with NAC, hCG, EGCG and somatostatin," Clinical & Experimental Metastasis, 1999, pp. 739, vol. 17.

Arima et al., "IL-2-Induced Growth of CD8+ T Cell Prolymphocytic Leukemia Cells Mediated by NF-kappaB Induction and IL-2 Receptor alpha Expression," Leukemia Research, 1998, pp. 265-273, vol. 22, No. 3.

Baeuerle et al., "Function and Activation of NF-κB in the Immune System," Annu. Rev. Immunol., 1994, pp. 141-179, vol. 12.

Bethea et al., "Traumatic Spinal Cord Injury Induces Nuclear Factor-κB Activation," The Journal of Neuroscience, May 1, 1998, pp. 3251-3260, vol. 18, No. 9.

Blackwell et al., "The Role of Nuclear Factor-κB in Cytokine Gene Regulation," Am. J. Respir. Cell Mol. Biol., 1997, pp. 3-9, vol. 17.

Bodfish et al., "Treating the Core Features of Autism: Are We There Yet?" Mental Retardation and Developmental Disabilities Research Reviews, 2004, pp. 318-326, vol. 10.

Bradham et al., Activation of nuclear factor- κB during orthotopic liver transplantation in rats is protective and does not require Kuppfer cells, Liver Transplantation and Surgery, Jul. 1999, pp. 282-293, vol. 5, No. 4.

Brown et al., "Two Forms of NF-kappaB1 (p. 105/p. 50) in Murine Macrophages: Differential Regulation by Lipopolysaccharide, Interleukin-2, and Interferon-gamma," Journal of Interferon and Cytokine Research, 1997, pp. 295-306, vol. 17.

Christman et al., "Nuclear factor kappaB: a pivotal role in the systemic inflammatory response syndrome and new target for therapy," Intens Care Med, 1998, pp. 1131-1138, vol. 24.

Connelly et al., "Biphasic Regulation of NF-κB Activity Underlies the Pro- and Anti-inflammatory Actions of Nitric Oxide," The Journal of Immunology, 2001, pp. 3873-3881, 166, The American Association of Immunologists, USA.

Cook et al., Modified total lymphoid irradiation and low dose coricosteroids in progressive multiple sclerosis, Journal of Neurological Sciences, vol. 152, pp. 172-181, 1997.

Cui et al., Am. J. Physiol. Integr. Comp. Physiol., 2004, pp. R699-R709, vol. 286.

Dwinnell et al., Atlas of Diseases of the Kidney, Blackwell Sciences, 1999, pp. 12.1-12.12, Ch. 12.

Emmel et al., "Cyclosporin A Specifically Inhibits Function of Nuclear Proteins Involved in T Cell Activation," Science, Dec. 22, 1989, pp. 1617-1620, vol. 246.

Epinat et al., "Diverse agents act at multiple levels to inhibit the Rel/NF-kappaB signal transduction pathway," Oncogene, 1999, pp. 6896-6909, vol. 18.

Fassio et al., Transforming Growth Factor Alpha and Its Receptor in Neural Retina, Investigative Ophthalmology & Visual Science, Sep. 1989, pp. 1916-1922, vol. 30, No. 9.

Faust et al., "Disseminated intravascular coagulation and purpura fulminans secondary to infection," Bailliere's Clinical Haematology, 2000, 179-197, vol. 13. No. 2.

Flores et al., NFkappaB and AP-1 DNA binding activity in patients with multiple sclerosis. J. Neuroimmunol. vol. 135, No. 1-2, pp. 141-147, Feb. 2003.

Friedlander, "Tackling anthrax," Nature, Nov. 8, 2001, pp. 160-161, vol. 414.

GenBank Accession No. NP_000728, GI: 4502789, publicly available Apr. 2007.

Han et al., Cholecystokinin induction of mob-1 chemokine expression in pancreatic acinar cells requires NF-kappaB activation, American Journal of Physiology, Jul. 1999, vol. 277, pp. C74-C82.

Ichiyama et al., Systemically administered alpha-melanocyte-stimulating peptides inhibit NF-kappaB activation in experimental brain inflammation, Brain Research, Jul. 1999, pp. 31-37, vol. 836.

Ivanov et al., "Hemoglobin as a Source of Endogenous Bioactive Peptides: The Concept of Tissue-Specific Peptide Pool," Biopolymers, 1997, pp. 171-188, vol. 39.

Jimenez-Garza et al., "Early Effects of Modulating Nuclear factor-kappaB Activation on Traumatic Spinal Cord Injury in Rats," Ann. N.Y Acad. Sci., 2005, pp. 148-150, vol. 1053.

Jyonouchi et al., "Proinflammatory and regulatory cytokine production associated with innate and adaptive immune responses in children with autism spectrum disorders and developmental regression," J Neuroim., 2001, pp. 170-179, vol. 120.

Kachra et al., "Low Molecular Weight Components but Not Dimeric HCG Inhibit Growth and Down-Regulate AP-1 Transcription Factor in Kaposi's Sarcoma Cells," Endocrinology, 1997, pp. 4038-4041, vol. 138, No. 9.

Kalns et al., Biochem. Biophys. Res. Comm., 2002, pp. 41-44, vol. 292.

Kalns et al., Biochem. Biophys. Res. Comm., 2002, pp. 506-509, vol. 297.

Kanungo et al., "Advanced Maturation of Heteropneustes Fossilis (Bloch) by Oral Administration of Human Chorionic Gonadotropin," J. Adv. Zool., 1999, pp. 1-5, vol. 20.

Keeton and Gould, Biological Science, 5th Ed., New York, W.W. Norton & Company, Inc. 1993, p. 4.

Keller et al., "Human Chorionic Gonadotropin (hCG) Is a Potent Angiogenic Factor for Uterine Endothelial Cells in Vitro," PLACENTA, Jul. 1999, pp. A37, vol. 20, No. 5-6.

Khan et al., "Inhibition of Diabetes in NOD Mice by Human Pregnancy Factor," Human Immunology, Dec. 2001, pp. 1315-1323, vol. 62, No. 12.

Khan et al., "Inhibition of Septic Shock in Mice by an Oligopeptide From the β-Chain of Human Chorionic Gonadotrophin Hormone," Human Immunology, Jan. 2002, pp. 1-7, vol. 63, No. 1.

Khavinson et al, Gerontological Aspects of Genome Peptide Regulation, 2005, S. Karger AG, Basel, Switzerland.

Khavinson et al., "Effects of Livagen Peptide on Chromatin Activation in Lymphocytes from Old People," Bulletin of Experimental Biology and Medicine, Oct. 2002, pp. 389-392, vol. 134, No. 4.

Khavinson et al., "Effects of Short Peptides on Lymphocyte Chromatin in Senile Subjects," Bulletin of Experimental Biology and Medicine, Jan. 2004, pp. 78-81, vol. 137, No. 1.

Khavinson et al., "Epithalon Peptide Induces Telomerase Activity and Telomere Elongation in Human Somatic Cells," Bulletin of Experimental Biology and Medicine, Jun. 2003, pp. 590-592, vol. 135, No. 6.

Khavinson et al., "Inductive Activity of Retinal Peptides," Bulletin of Experimental Biology and Medicine, Nov. 2002, pp. 482-484, vol. 134, No. 5.

Khavinson et al., "Mechanisms Underlying Geroprotective Effects of Peptides," Bulletin of Experimental Biology and Medicine, Jan. 2002, pp. 1-5, vol. 133, No. 1.

Khavinson et al., "Peptide Promotes Overcoming of the Division Limit in Human Somatic Cell," Bulletin of Experimental Biology and Medicine, May 2004, pp. 503-506, vol. 137, No. 5.

Kidd et al., "Autism, An Extreme Challenge to Integrative Medicine. Part II: Medical Management," Alternative Medicine Review, 2002, pp. 472-499, vol. 7, No. 6.

Kronfol et al., "Cytokines and the Brain: Implications for Clinical Psychiatry," Am. J. Psychiatry, May 2000, pp. 683-694, vol. 157, No. 5.

Lang et al., "Induction of apoptosis in Kaposi's sarcoma spindle cell cultures by the subunits of human chorionic gonadtropin," AIDS, 1997, pp. 1333-1340, vol. 11, No. 11.

Li et al., "NF-kappaB Regulation in the Immune System," Nature Reviews/Immunology, Oct. 2002, pp. 725-734, vol. 2.

Lunardi-Iskandar et al., "Effects of a urinary factor from women in early pregnancy on HIV-a, SIV and associated disease," Nature Medicine, pril 1998, pp. 428-434, vol. 4, No. 4.

Malek-Ahmadi, P., "Role of Cytokines in Psychopathology: Therapeutic Implications," Drug News Prospects, Jun. 1998, pp. 271-276, vol. 11, No. 5.

Malyak et al., Characterization of a Low Molecular Weight Isoform of IL-1 Receptor Antagonist, The Journal of Immunology, 1998, pp. 1997-2003, vol. 161.

McBean et al., "Rodent Models of Global Cerebral Ischemia: A Comparison of Two-Vessel Occlusion and Four-Vessel Occlusion," Gen. Pharmac., 1998, pp. 431-434, vol. 30, No. 4.

McDonald et al., "Interleukin-15 (IL-15) Induces NF-kappaB Activation and IL-8 Production in Human Neutrophils," Blood, Dec. 15, 1998, pp. 4828-4835, vol. 92, No. 12.

MedlinePlus, Medical Encyclopedia: autoimmune disorders (www.nlm.gov/medlineplus/ency/article/000816.htm), (2005).

Medzhitov, "Toll-like Receptors and Innate Immunity," Nature Reviews/Immunology, Nov. 2001, pp. 135-145, vol. 1.

Merck Manual, 17th ed. 1999, pp. 1145-1146, 1841-1848, 2539, 2551.

Merriam-Webster Medical Dictionary, 1994, p. 82.

Moayeri et al., Journal of Clinical Investigation, Sep. 2003, pp. 670-682, vol. 112, No. 5.

Morozov et al., "Natural and Synthetic Thymic Peptides as Therapeutics for Immune Dysfunction," Int. J. Immunopharmac., 1997, pp. 501-505, vol. 19, No. 9/10.

Muchmore et al., "Immunoregulatory Properties of Fractions from Human Pregnancy Urine: Evidence that Human Chorionic Gonadotropin is not Responsible," The Journal of Immunology, Mar. 1997, pp. 881-886, vol. 118, No. 3.

Muchmore et al., "Purification and Characterization of a Mannose-Containing Disaccharide Obtained from Human Pregnancy Urine," Journal of Experimental Medicine, Dec. 1984, pp. 1672-1685, vol. 160.

Neely et al., "Then and now: Studies using a burned mouse model reflect trends in burn research over the past 25 years," Burns, 1999, pp. 603-609, vol. 25.

Ngo et al., The protein folding problem and tertiary structure prediction, 1994, pp. 492-494.

Ohlsson et al., Interleukin-1 Receptor Antagonist Reduces Mortality from Endotoxin Shock, Nature, Dec. 6, 1990, pp. 550-552, vol. 348.

Oka et al., Immunosuppression in organ transplantation, Japanese Journal of Pharmacology, vol. 71, No. 2, pp. 89-100, Jun. 1996.

Olszyna et al., Levels of Inhibitors of Tumor Necrosis Factor Alpha and Interleukin 1b in Urine and Sera of Patients with Urosepsis, Infection and Immunity, Aug. 1998, pp. 3527-3534.

Patil et al., "The Study of the Effect of Human Chorionic Gonadotrophic (HCG) Hormone on the Survival of Adrenal Medulla Transplant in Brain. Preliminary Study," ACTA Neurochir (WIEN), 1987, pp. 76-78, vol. 87.

PCT International Search Report, International Application No. PCT/NL02/00639, mailed Aug. 4, 2003.

PCT International Search Report, PCT/EP2005/003707, dated Jul. 5, 2005.

PCT International Search Report, PCT/NL01/00259, dated Dec. 18, 2001.
Pellizzari et al., FEBS Letters, 1999, pp. 199-204, vol. 462.
Rohrig et al., "Growth-stimulating Influence of Human Chorionic Gonadotropin (hCG) on Plasmodium falciparum in vitro," Zentralblatt Bakt, 1999, pp. 89-99, vol. 289.
Samaniego et al., "Induction of Programmed Cell Death in Kaposi's Sarcoma Cells by Preparations of Human Chorionic Gonadotropin," Journal of the National Cancer Institute, Jan. 20, 1999, pp. 135-143, vol. 91, No. 2.
Slater et al., "Decreased Mortality of Murine Graft-Versus-Host Disease by Human Chorionic gonadotropin," Transplantation, Jan. 1977, pp. 103-104, vol. 23, No. 1.
Smith et al., "Recent developments in drug therapy for multiple sclerosis," Multiple Sclerosis, 1999, pp. 110-120, vol. 5.
Tak et al., "NF-kappaB: a key role in inflammatory diseases," J Clin Invest., 2001, pp. 7-11, vol. 107.
Tan et al., "The role of activation of nuclear factor-kappa B of rat brain in the pathogenesis of experimental allergic encephalomyelitis," Acta Physiol Sinica, 2003, pp. 58-64, vol. 55.
Tovey et al., "Mucosal Cytokine Therapy: Marked Antiviral and Antitumor Activity," J. Interferon Cytokine Res., 1999, pp. 911-921, vol. 19.
Traystman, R., "Animal Models of Focal and Global Cerebral Ischemia," ILAR Journal, 2003, pp. 85-95, vol. 44, No. 2.
Weinberger et al., "Mechanisms Mediating the Biologic Activity of Synthetic Proline, Glycine, and Hydroxyproline Polypeptides in Human Neurophils," Mediators of Inflammation, 2005, pp. 31-38, vol. 1.
Wulczyn et al., "The NF-κB/Rel and IkB gene families: mediators of immune response and inflammation," J. Mol. Med., 1996, pp. 749-769, vol. 74, No. 12.
Yamamoto et al., "Role of the NF-κB Pathway in the Pathogenesis of Human Disease States," Current Molecular Medicine, Jul. 2001, pp. 287-296, vol. 1, No. 3.
Yang et al., "Increased cortical nuclear factor κB (NF-κB) DNA binding activity after traumatic brain injury in rats," Neuroscience Letters, 1995, pp. 101-104, vol. 197.
Zhou et al., Transplantation tolerance in NF-κB-impaired mice is not due to regulation but is prevented by transgenic expression of Bcl-xL. The Journal of Immunology, vol. 174, No. 6, pp. 3447-3453, Mar. 2005.
Barton et al., Protective Role of Interleukin 6 in the Lipopolysaccharide-Galactosamine Septic Shock Model, Infection and Immunity, Apr. 1993, pp. 1496-1499, vol. 61, No. 4.
Bastin et al., Salt Selection and Optimisation Procedures for Pharmaceutical new Chemical Entities, Org. Proc. Res. Develop. 2000, pp. 427-435, vol. 4.
Baud et al., Signaling by proinflammatory cytokines: oligomerization of TRAF2 and TRAF6 is sufficient for JNK and IKK activation and target gene induction via an amino-terminal effector domain, Genes & Development, May 1999, pp. 1297-1308, vol. 13.
Borchardt, RT, Optimizing oral absorption of peptides using prodrug strategies, Journal of Controlled Release, Nov. 1999, pp. 231-238, vol. 62.
Burdelya et al., An agonist of toll-like receptor 5 has radioprotective activity in mouse and primate models, Abstract, Science, Apr. 11, 2008, pp. 226-230, vol. 320, No. 5873.
Burdelya et al., NF-kappaB activating proteins as radioprotectants: Derivatives of Flagellin from Salmonella protect mice from hematopoietic and gastrointestinal Radiation Syndromes. Cleveland Biolabs, Inc.
Capizzi, Investigational New Drugs, 1996, 14:249-256.
Clerici et al., Single-cell analysis of cytokine production shows different immune profiles in multiple sclerosis patients with active or quiescent disease. Journal of Neuroimmunology, vol. 121, pp. 33-101. 2001.
Cleveland BioLabs, Inc., Radiation Antidote for Defense, (visited Apr. 16, 2008) <http://www.cbiolabs.com/Applications.php.
Cohen, Int J. Radiat. Oncol. Biol. Phys., 1987, pp. 251-258, vol. 13.
Corvino et al., Availability, stability and sterility of pralidoxime for mass casualty use, Abstract, Ann Emerg Med., Mar. 2006, pp. 272-277, vol. 47, No. 3.

Daemen et al., Ischemia-reperfusion-induced IFN-gamma up-regulation: involvement of IL-12 and IL-13, The Journal of Immunology, 1999, pp. 5506-5510, vol. 162.
De Saizieu et al., Journal of Bacteriology, vol. 182, No. 17, pp. 4696-4703, Sep. 2000.
Dechend et al., Oncogene, vol. 18, pp. 3316-3323, 1999.
Dietrich et al., Postischemic hypothermia and IL-10 treatment provide long-lasting neuroprotection of CA1 hippocampus following transient global ischemia in rats. Experimental Neurology, 1999, pp. 444-450, vol. 158.
Donnahoo et al., Early kidney TNF-alpha expression mediates neutrophil infiltration and injury after renal ischemia-reperfusion, American Journal of Physiology, Sep. 1999, pp. R922-R929, vol. 277, No. 3, Pt. 2.
Eckardt et al., Hypoxia-induced accumulation of erythropoietin mRNA in isolated hepatocytes is inhibited by protein kinase C, Pflugers Archiv., 1994. pp. 21-30. vol. 426.
Engles et al., Exogenous human recombinant interleukin-10 attenuates hindlimb ischemia-reperfusion injury, Journal of Surgical Research, 1997, pp. 425-428. vol. 69.
Garkavtsev et al.. Suppression of the novel growth inhibitor p33ING1 promotes neoplastic transformation, Nature Publishing Group, Dec. 14, 1996, pp. 415-420.
Garkavtsev et al., The candidate tumour suppressor p33ING1 cooperates with p53 in cell growth control, Nature, Jan. 15, 1998, pp. 295-298, vol. 391.
Gould, Salt selection for basic drugs, Int. J. Pharm., 1986, pp. 201-217, vol. 33.
Gudkov et al., The role of p53 in determining sensitivity to radiotherapy, Nature Reviews, Feb. 2003, pp. 117-129, vol. 3.
Gudkov, Andrei V., Cancer drug discovery: the wisdom of imprecision, Nature Medicine, Dec. 2004, 1298-00, vol. 10, No. 12.
Gudkov, Andrei V., Converting p53 from a killer into a healer, Nature Medicine, Nov. 2002, pp. 1196-1198. vol. 8. No. 11.
http://www.rxlist.com/cgi/generic/chorionic.htm—RX List.com entry for hCG/Pregnyl, (2008).
Hierholzer et al., Essential role of induced nitric oxide in the initiation of the inflammatory response after hemorrhagic shock, J. Exp. Med., Mar. 1998, pp. 917-928, vol. 187, No. 6.
Huang et al., Ischemia-reperfusion and immediate T cell responses, Cellular Immunology, 2007, pp. 4-11, vol. 248.
Husek et al., Rapid screening of urinary proline-hydroxyproline dipeptide in bone turnover studies, Abstract, J. Chromatogr B Analyt Technol Biomed Life Sci., Feb. 5, 2002, pp. 169-174, vol. 767, No. 1.
Iyer et al., The transcriptional program in the response of human fibroblasts to serum, Science, Jan. 1999, pp. 83-87, vol. 283, No. 5398.
Kato et al., Reduced hepatic ischemia/reperfusion injury by IL-4: potential anti-inflammatory role of STAT6, Inflammation Research, Jun. 2000, pp. 275-279, vol. 49, No. 6.
Lane et al., Interleukin-10 reduces the systemic inflammatory response in a murine model of intestinal ischemia/reperfusion. Surgery, 1997, pp. 288-294, vol. 122, No. 2.
Le Moine et al., Cold liver ischemia-reperfusion injury critically depends on liver T cells and is improved by donor pretreatment with interleukin 10 in mice, Hepatology, 2000, pp. 1266-1274, vol. 31, No. 6.
Lin et al., The Journal of Biological Chemistry, vol. 270, No. 24, pp. 14255-14258, Jun. 1995.
Lutterova et al., Marked difference in tumor necrosis factor-alpha expression in warm ischemia- and cold ischemia-reperfusion of the rat liver, Cryobiology, 2000, pp. 301-314, vol. 41.
Manna et al., Human chorionic gonadotropin suppresses activation of nuclear transcription factor-kappa B and activator protein-1 induced by tumor necrosis factor, The Journal of Biological Chemistry, May 2000, pp. 13307-13314, vol. 275, No. 18.
NCBI Accession No. AAI06724, version Oct. 6, 2006.
Padmos et al., A discriminating messenger RNA signature for bipolar disorder formed by an aberrant expression of inflammatory genes in monocytes, Arch Gen Psychiatry, Apr. 2008, pp. 395-407, vol. 65, No. 4.

Pan et al., Bradykinin Stimulates NF-κB Activation and Interleukin 1β Gene Expression in Cultured Human Fibroblasts, J. Clin. Invest., Nov. 1996, pp. 2042-2049, vol. 98, No. 9, The American Society for Clinical Investigation, Inc.

Partial European Search Report for 02 763 111.8 dated Nov. 23, 2007.

PCT International Search Report and Written Opinion, PCT/NL2007/050092, dated Jul. 6, 2007.

PCT International Search Report, PCT/CA97/00568, dated Apr. 30, 1998.

Qin et al., Nuclear Factor κB Nuclear Translocation Upregulates c-Myc and p53 Expression during NMDA Receptor-Mediated Apoptosis in Rat Striatum, The Journal of Neuroscience, May 15, 1999, pp. 4023-4033, vol. 19, No. 10.

Quillan et al., Combinatorial diffusion assay used to identify topically active melanocyte-stimulating hormone receptor antagonists, PNAS, Mar. 1995, pp. 2894-2898, vol. 92, USA.

"RDT&E Budget item justification sheet" StartDateMarker 1999, EndDateMarker Retrieved from the Internet: URL:http://www.dtic.mil/descriptivesum/Y2000/OSD/PE0602787D.pdf>.

Redon et al., Global variation in copy number in the human genome, Nature, Nov. 23, 2006. pp. 444-454. vol. 444.

Riera et al., Neutrophils accentuate renal cold ischemia-reperfusion injury. Dose-dependent protective effect of platelet-activating factor receptor antagonist, The Journal of Pharmacology and Experimental Therapeutics. 1997, pp. 786-794, vol. 280, No. 2.

Rodriguez et al., Expression of human HLA-B27 transgene alters susceptibility to murine theiler's virus-induced demylenination, 1991, vol. 146, pp. 2596-2602.

Selzman et al., Interleukin-10 inhibits postinjury tumor necrosis factor-mediated human vascular smooth muscle proliferation, Journal of Surgical Research, 1998, pp. 352-356, vol. 80.

Sharma, Septic Shock, (visited Sep. 27, 2007 <http://www.emedicine.com/MED/topic2101.htm>.

Sovak et al., Aberrant nuclear factor-kappa B/Rel expression and the pathogenesis of breast cancer, The Journal of Clinical Investigation, Dec. 1997, pp. 2952-2960, vol. 100, No. 12.

Strom et al., Small-molecule inhibitor of p53 binding to mitochondria protects mice from gamma radiation, Nature Chemical Biology, Sep. 2006, pp. 474-479, vol. 2. No. 9.

Szinicz, L., History of chemical and biological warfare agents, Abstract, Toxicology. Oct. 30. 2005, pp. 167-181, vol. 214, No. 3.

Thibonnier et al., Cytoplasmic and nuclear signaling pathways of V1-vascular vasopressin receptors, Regulatory Peptides, 1993, pp. 79-84, vol. 45.

Valore et al., Human b-Defensin-1: An antimicrobial Peptide of Urogenital Tissues, J. Clin. Invest., Apr. 1998, pp. 1633-1642, vol. 101, No. 8.

Wallraff et al., Urinary Excretion of Amino Acids in Pregnancy, J. Clinc. Invest., 1950, pp. 1542-1544, vol. 29.

Wu et al., Gonadotropin-Releasing Hormone (GNRH) Cleavage Products are Involved in the Regulation of GNRH Gene Expression in the GT1-7 Neuronal Cell Line. Society for Neuroscience Abstracts, Nov. 4, 2000, pp. 7.8, XP009091566, vol. 26, No. 1-2.

Office Action for U.S. Appl. No. 10/409,032 dated May 17, 2007.
Office Action for U.S. Appl. No. 10/409,032 dated Jan. 15, 2008.
Office Action for U.S. Appl. No. 10/409,032 dated Aug. 20, 2008.
Office Action for U.S. Appl. No. 10/409,032 dated Jun. 1, 2009.
Office Action for U.S. Appl. No. 11/037,972 dated Oct. 11, 2007.
Office Action for U.S. Appl. No. 11/037,972 dated Jun. 4, 2008.
Office Action for U.S. Appl. No. 11/037,972 dated Dec. 12, 2008.
Office Action for U.S. Appl. No. 11/446,458 dated Jun. 15, 2007.
Office Action for U.S. Appl. No. 11/446,458 dated Jan. 11, 2008.
Office Action for U.S. Appl. No. 11/446,458 dated Jul. 28, 2008.
Office Action for U.S. Appl. No. 11/446,458 dated Sep. 2, 2008.
Office Action for U.S. Appl. No. 11/446,458 dated Mar. 6, 2009.
Office Action for U.S. Appl. No. 11/481,423 dated Jan. 31, 2008.
Office Action for U.S. Appl. No. 11/481,423 dated Jul. 24, 2008.
Office Action for U.S. Appl. No. 11/481,423 dated Apr. 16, 2009.
Office Action for U.S. Appl. No. 11/593,329 dated Apr. 6, 2009.
Office Action for U.S. Appl. No. 11/600,294 dated Apr. 3, 2009.
Office Action for U.S. Appl. No. 11/600,294 dated Dec. 17, 2009.
Office Action for U.S. Appl. No. 11/715,314 dated Feb. 26, 2009.
Office Action for U.S. Appl. No. 11/715,314 dated Aug. 14, 2009.
Office Action for U.S. Appl. No. 11/975,284 dated Dec. 29, 2008.
Office Action for U.S. Appl. No. 11/975,284 dated Oct. 1, 2009.
Office Action for U.S. Appl. No. 11/982,292 dated May 18, 2009.
Office Action for U.S. Appl. No. 11/982,292 dated Aug. 28, 2009.
Notice of Allowance for U.S. Appl. No. 11/481,423 dated Nov. 16, 2009.

U.S. Appl. No. 12/001,035, filed Dec. 6, 2007, Khan et al., Gene Regulator.

U.S. Appl. No. 12/074,020, filed Feb. 29, 2008, Khan et al., Oligopeptide Treatment of Ischemia-Reperfusion Injury.

U.S. Appl. No. 12/288,935, filed Oct. 24, 2008, Benner et al., Control of Radiation Injury.

U.S. Appl. No. 12/386,135, filed Apr. 14, 2009, Khan et al., Gene Regulator.

U.S. Appl. No. 12/069,401, filed Feb. 8, 2008, Khan et al., Immunoregulatory Compositions.

U.S. Appl. No. 12/386,061, filed Apr. 9, 2009, Khan et al., Methods and Uses for Protein Breakdown Products.

U.S. Appl. No. 12/383,849, filed Mar. 27, 2009, Khan et al., Compositions for Mucosal and Oral Administration Comprising HCG Fragments.

U.S. Appl. No. 11/975,284, filed Oct. 17, 2007, Khan et al., Treatment for Tumors.

U.S. Appl. No. 12/460,317, filed Jul. 15, 2009, Benner et al., Control of Radiation Injury.

U.S. Appl. No. 11/981,491, filed Oct. 30, 2007, Khan et al., Treatment of Iatrogenic Disease.

U.S. Appl. No. 11/986,043, filed Oct. 30, 2007, Khan et al., Peptide Compositions.

U.S. Appl. No. 11/982,292, filed Oct. 31, 2007, Khan et al., Treatment of Neurological Disorders.

U.S. Appl. No. 11/982,293, filed Oct. 31, 2007, Khan et al., Stratification.

U.S. Appl. No. 11/715,314, filed Mar. 7, 2007, Benner et al., Control of Radiation Injury.

U.S. Appl. No. 12/083,472, filed Apr. 11, 2008, Drexhage et al., Method to Diagnose or Screen for Inflammatory Diseases.

U.S. Appl. No. 12/069,741, filed Feb. 12, 2008, Khan et al., Treatment of Trauma-Hemorrhage With Short Oligopeptides.

* cited by examiner

Hemorrhagic Shock model (HS)
( * = time of administration peptide A, B or C in the peptide groups)

SEQUENCE LISTING

```
<160> NUMBER OF SEQ ID NOS: 29

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1
```

Leu Gln Gly Val
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Gln Gly Val
1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Leu Gln Gly Ala
1

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Val Leu Pro Ala Leu Pro
1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Leu Pro Ala Leu Pro
1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ala Pro Ala Leu Pro
1               5

<210> SEQ ID NO 7
<211> LENGTH: 7
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 7

Ala Leu Pro Ala Leu Pro Gln
 1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Val Leu Pro Ala Ala Pro Gln
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Leu Pro Ala Leu Ala Gln
 1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Ala Gly Val
 1

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Leu Ala Ala Leu Pro
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Leu Pro Ala Leu Ala
 1               5
```

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Val Leu Pro Ala Leu Pro Gln
  1               5

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Val Leu Ala Ala Leu Pro Gln
  1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Val Leu Pro Ala Leu Pro Ala
  1               5

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gly Val Leu Pro Ala Leu Pro
  1               5

<210> SEQ ID NO 17
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Gln Gly Val Leu Pro Ala Leu Pro Gln Val Val Cys
  1               5                  10

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Leu Pro Gly Cys Pro Arg Gly Val Asn Pro Val Val Ser
  1               5                   10

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Leu Pro Gly Cys
  1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Thr Arg Val
  1

<210> SEQ ID NO 21
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Val Leu Pro Ala Leu Pro Gln Val Val Cys
  1               5                   10

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Leu Gln Gly Val Leu Pro Ala Leu Pro Gln
  1               5                   10

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gly Val Leu Pro Ala Leu Pro Gln
  1               5

<210> SEQ ID NO 24
<211> LENGTH: 38
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 24

Val Val Cys Asn Tyr Arg Asp Val Arg Phe Glu Ser Ile Arg Leu Pro
 1               5                  10                  15

Gly Cys Pro Arg Gly Val Asn Pro Val Val Ser Tyr Ala Val Ala Leu
            20                  25                  30

Ser Cys Gln Cys Ala Leu
        35

<210> SEQ ID NO 25
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Arg Pro Arg Cys Arg Pro Ile Asn Ala Thr Leu Ala Val Glu Lys Glu
 1               5                  10                  15

Gly Cys Pro Val Cys Ile Thr Val Asn Thr Thr Ile Cys Ala Gly Tyr
            20                  25                  30

Cys Pro Thr
        35

<210> SEQ ID NO 26
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Lys Ala Pro Pro Pro Ser Leu Pro Ser Pro Ser Arg Leu Pro Gly
 1               5                  10                  15

Pro Ser

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ser Ile Arg Leu Pro Gly Cys Pro Arg Gly Val Asn Pro Val Val Ser
 1               5                  10                  15

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
agctcagagg gggactttcc gagag                                          25
```

```
-continued

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Val Val Cys
  1
```

US 7,786,084 B2

TREATMENT OF BURNS

CROSS-REFERENCE TO RELATED APPLICATIONS

This application is a continuation-in-part of patent application Ser. No. 10/409,694, filed Apr. 8, 2003, now abandoned, which is a continuation-in-part of application Ser. No. 10/028,075, filed Dec. 21, 2001, now abandoned, the content of the entirety of each of which are incorporated by this reference.

TECHNICAL FIELD

The current invention relates to the body's innate way of modulation of important physiological processes and builds on insights reported in WO99/59717, WO01/00259 and PCT/NL02/00639, the contents of the entirety of all of which are incorporated by this reference.

BACKGROUND

In the referenced earlier patent applications, small gene-regulatory peptides are described that are present naturally in pregnant women and are derived from proteolytic breakdown of placental gonadotropins such as human chorionic gonadotropin (hCG) produced during pregnancy. These peptides (in their active state often only at about 4 to 6 amino acids long) were shown to have unsurpassed immunological activity that they exert by regulating expression of genes encoding inflammatory mediators such as cytokines. Surprisingly, it was found that breakdown of hCG provides a cascade of peptides that help maintain a pregnant woman's immunological homeostasis. These peptides are nature's own substances that balance the immune system to assure that the mother stays immunologically sound while her fetus does not get prematurely rejected during pregnancy but instead is safely carried through its time of birth.

Where it was generally thought that the smallest breakdown products of proteins have no specific biological function on their own (except to serve as antigen for the immune system), it now emerges that the body in fact routinely utilizes the normal process of proteolytic breakdown of the proteins it produces to generate important gene-regulatory compounds, short peptides that control the expression of the body's own genes. Apparently, the body uses a gene-control system ruled by small broken down products of the exact proteins that are encoded by its own genes.

It is known that during pregnancy the maternal system introduces a status of temporary immuno-modulation which results in suppression of maternal rejection responses directed against the fetus. Paradoxically, during pregnancy, often the mother's resistance to infection is increased and she is found to be better protected against the clinical symptoms of various auto-immune diseases such as rheumatism and multiple sclerosis. The protection of the fetus can thus not be interpreted only as a result of immune suppression. Each of the above three applications have provided insights by which the immunological balance between protection of the mother and protection of the fetus can be understood.

We earlier showed that certain short breakdown products of hCG (i.e., short peptides which can easily be synthesized, if needed modified, and used as pharmaceutical composition) exert a major regulatory activity on pro- or anti-inflammatory cytokine cascades that are governed by a family of crucial transcription factors, the NFkappaB family which stands central in regulating the expression of genes that shape the body's immune response.

Most of the hCG produced during pregnancy is produced by cells of the placenta, the exact organ where cells and tissues of mother and child most intensely meet and where immuno-modulation is most needed to fight off rejection. Being produced locally, the gene-regulatory peptides which are broken down from hCG in the placenta immediately balance the pro- or anti-inflammatory cytokine cascades found in the no-mans land between mother and child. Being produced by the typical placental cell, the trophoblast, the peptides traverse extracellular space; enter cells of the immune system and exert their immuno-modulatory activity by modulating NFkappaB-mediated expression of cytokine genes, thereby keeping the immunological responses in the placenta at bay.

BRIEF SUMMARY OF THE INVENTION

It is herein postulated that the beneficial effects seen on the occurrence and severity of auto-immune disease in the pregnant woman result from an overspill of the hCG-derived peptides into the body as a whole; however, these effects must not be overestimated, as it is easily understood that the further away from the placenta, the less immuno-modulatory activity aimed at preventing rejection of the fetus will be seen, if only because of a dilution of the placenta-produced peptides throughout the body as a whole. However, the immuno-modulatory and gene-regulatory activity of the peptides should by no means only be thought to occur during pregnancy and in the placenta; men and women alike produce hCG, for example, in their pituitaries, and nature certainly utilizes the gene-regulatory activities of peptides in a larger whole.

Consequently, a novel therapeutic inroad is provided, using the pharmaceutical potential of gene-regulatory peptides and derivatives thereof. Indeed, evidence of specific up- or down-regulation of NFkappaB driven pro- or anti-inflammatory cytokine cascades that are each, and in concert, directing the body's immune response was found in silico in gene-arrays by expression profiling studies, in vitro after treatment of immune cells and in vivo in experimental animals treated with gene-regulatory peptides. Also, considering that NFkappaB is a primary effector of disease (A. S. Baldwin, J. Clin. Invest., 2001, 107:3-6), using the hCG derived gene-regulatory peptides offer significant potential for the treatment of a variety of human and animal diseases, thereby tapping the pharmaceutical potential of the exact substances that help balance the mother's immune system such that her pregnancy is safely maintained.

DETAILED DESCRIPTION OF THE INVENTION

Figure 1:
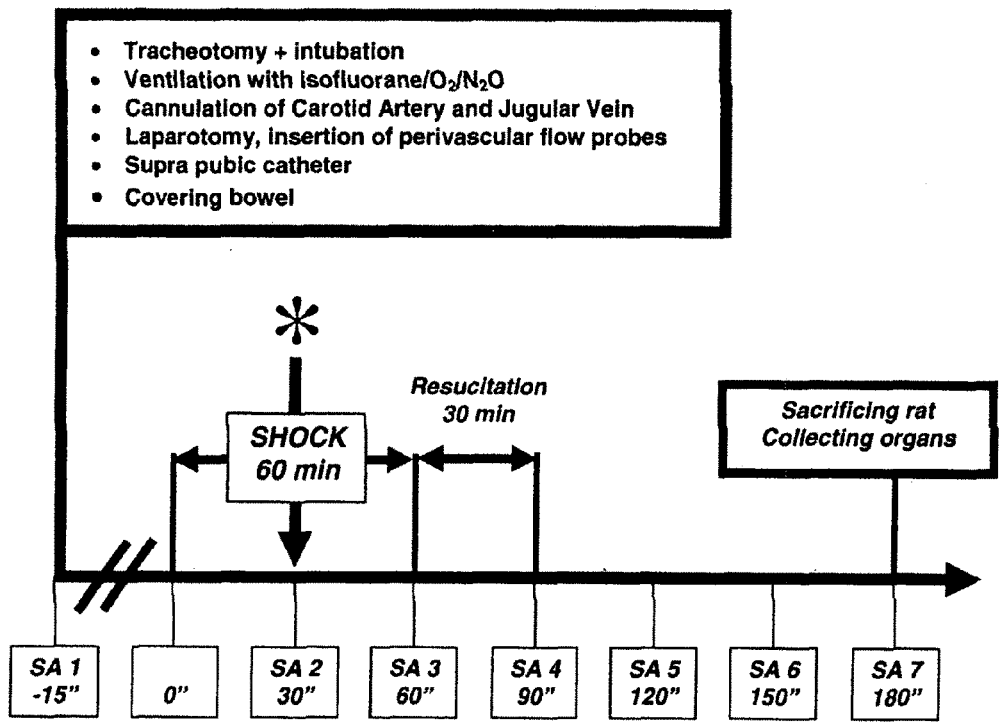
FIG. 1: Hemorrhagic Shock model (HS) (*=time of administration peptide A, B or C in the peptide groups).
Figure 2:
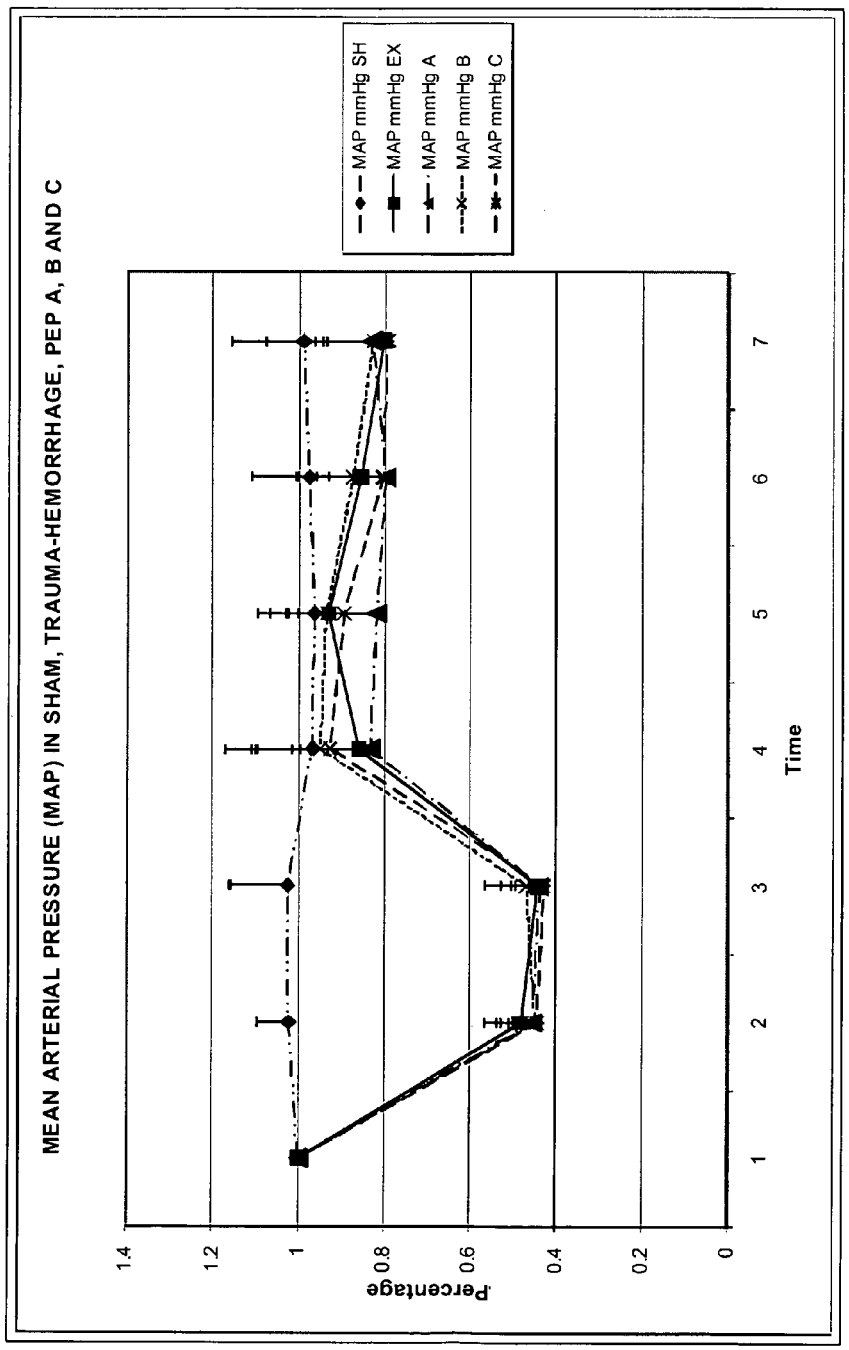
FIG. 2: Mean Arterial Pressure in sham, shock, and Peptide A, B and C experiments.
Figure 3:
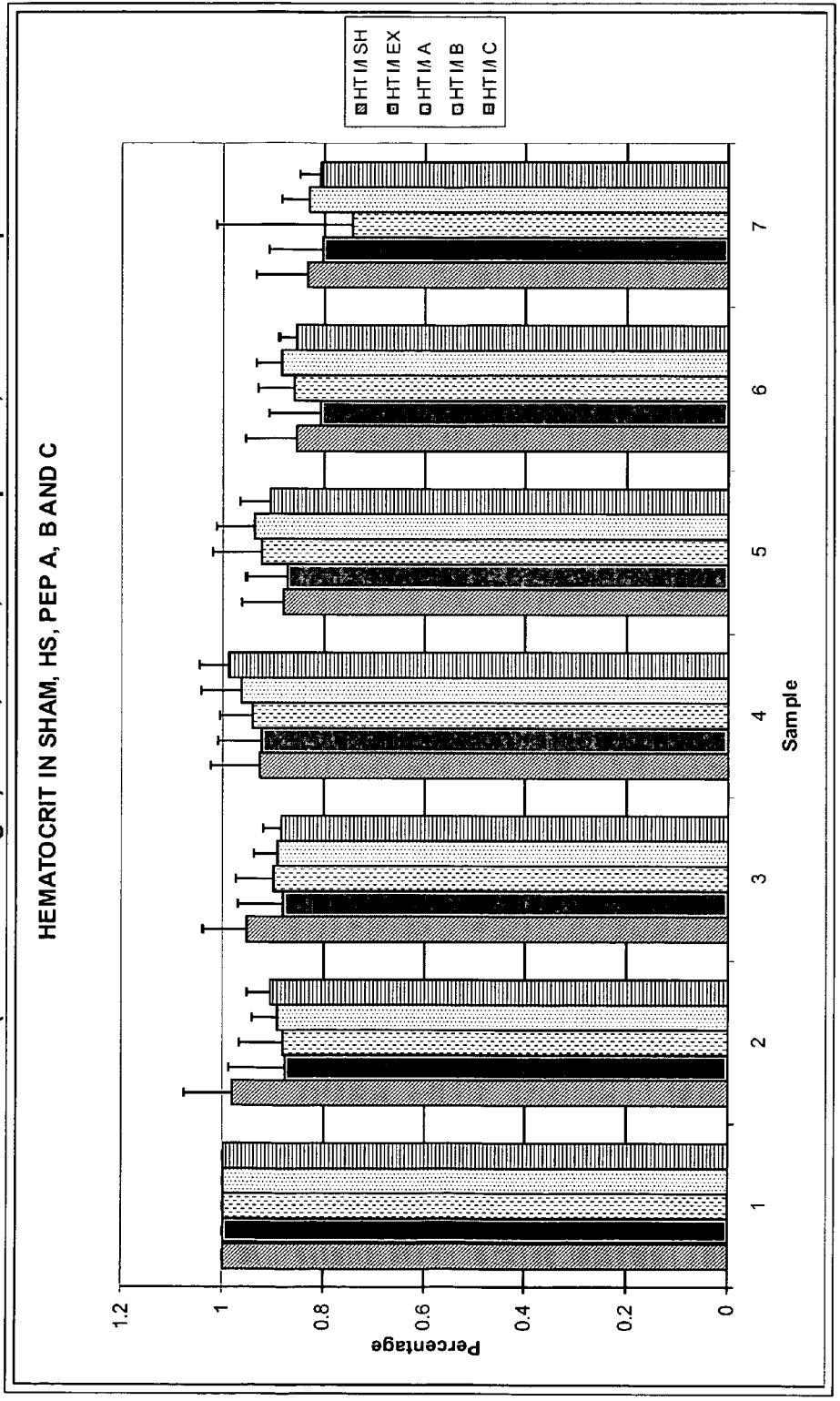
FIG. 3: Hematocrit in (from left to right) sham, shock, and Peptide A, B and C experiments.
Figure 4:
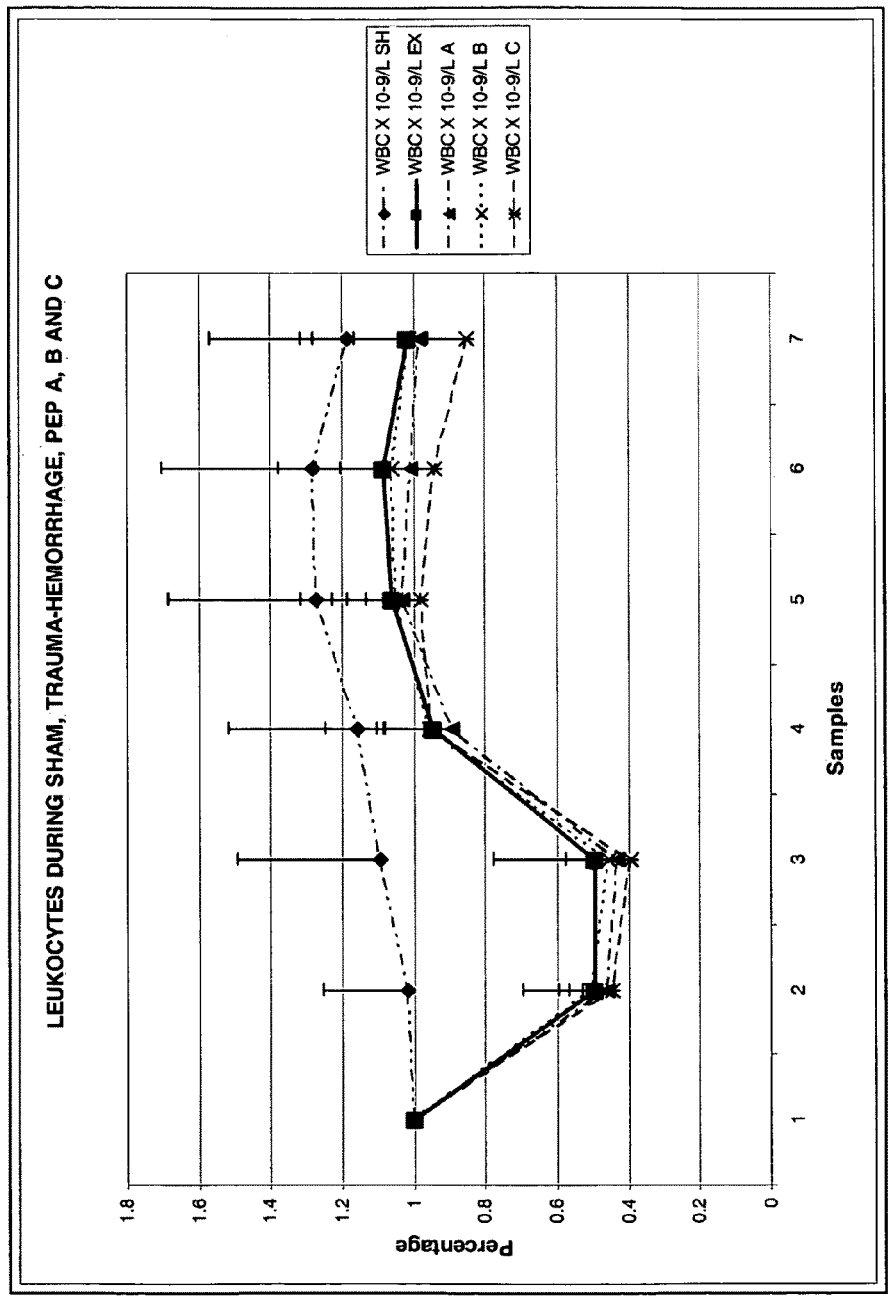
FIG. 4: Leukocytes during sham, trauma-hemorrhage, pep A, B and C experiments.
Figure 5:
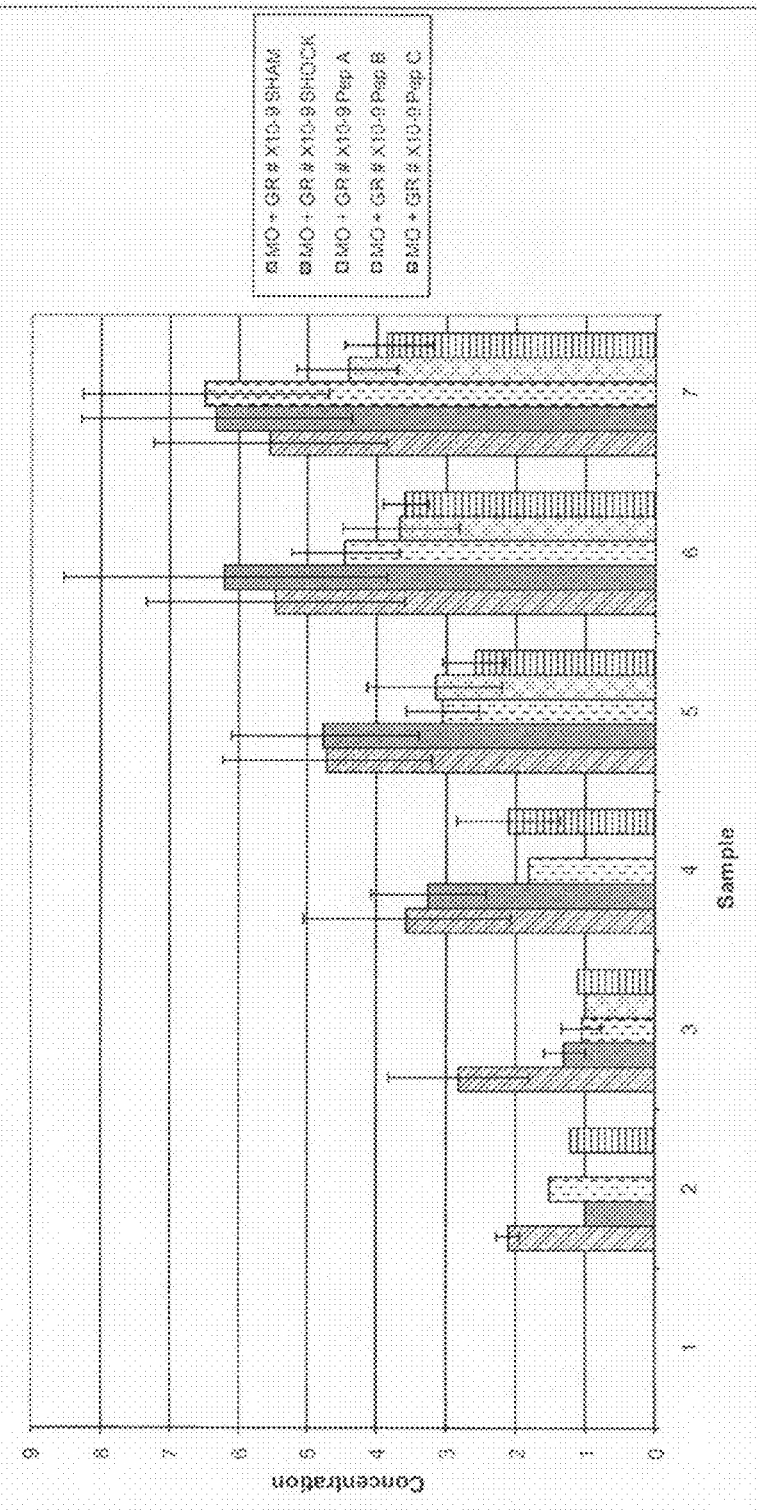
FIG. 5: Macrophages (MO) and granulocytes (GR) in (from left to right) sham, trauma-hemorrhagic shock, and Peptide A, B and C experiments.
Figure 6:
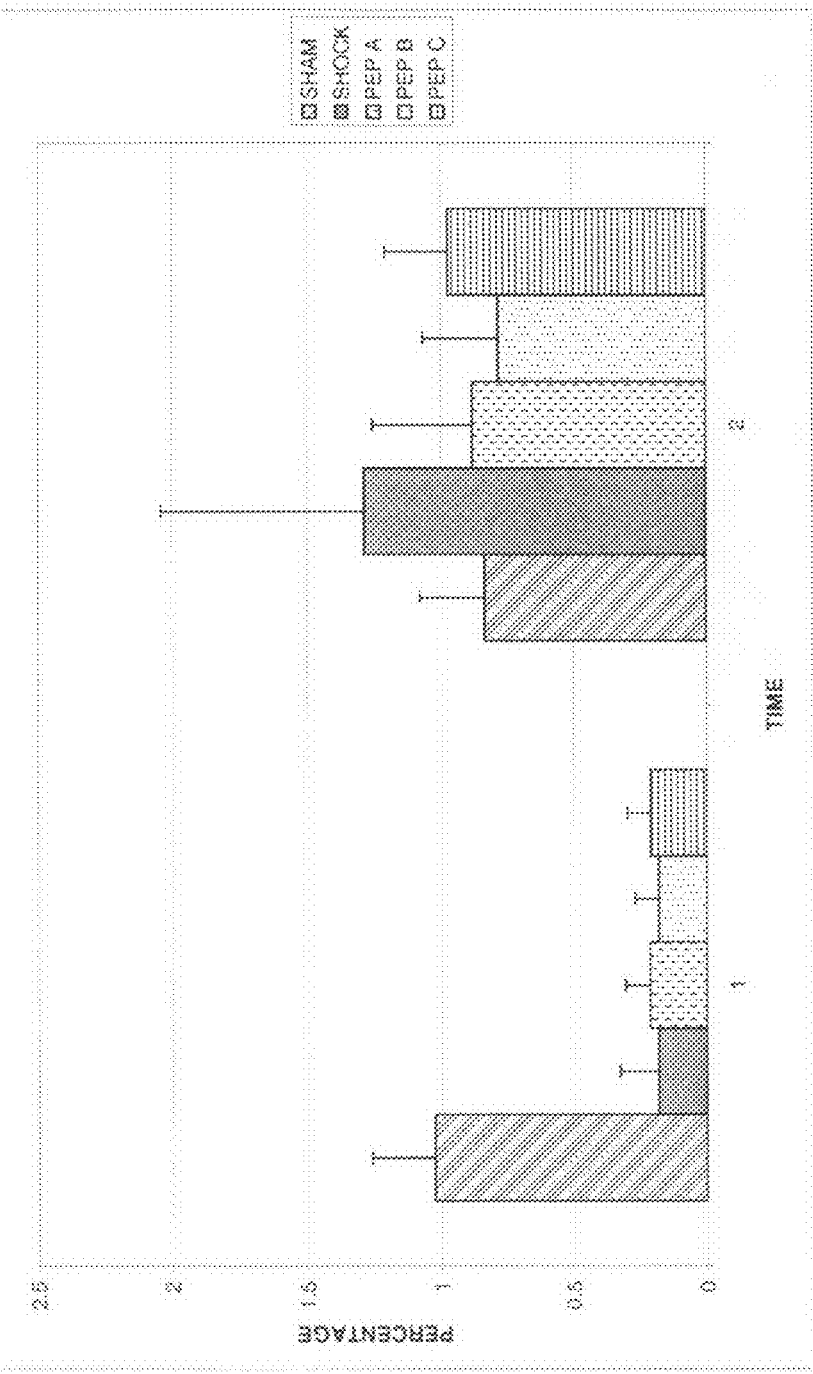
FIG. 6: Arterial blood flow in (from left to right) sham, shock, and Peptide A, B and C experiments.

This disclosure, in particular, relates to the treatment of burn injuries. Burn injuries are among the worst traumas which can happen to man. The larger a burn injury, the more severe the consequences and the higher the chance of an adverse outcome or even death. In The Netherlands alone, each year 40,000 people visit a general practitioner for treatment of a burn wound and 1,600 people require in-hospital care primarily for burns.

Approximately 80% of the burn accidents happen in or around the house, mainly in the kitchen. Scalds, usually due to hot water, are the most common cause of burns. Water at 60° C. will create a deep dermal or full-thickness burn in three seconds, and at 70° C. the same burn will occur in one second. The temperature of freshly brewed coffee from a percolator is generally about 80° C., which is hot enough to cause a full-thickness burn in less than one second. Children are particularly at high risk to burns. Hot beverages, particularly coffee and tea, are the predominant cause of scald burns in children. One study showed that 81% of the burn injuries in children under the age of 5 were due to scalds. Cooking oil, when hot enough to use for cooking, may be in the range of 150-180° C. and can consequently cause very severe burns.

Burns are estimated to affect >1.4 million people in the United States annually. Of this number, 54,000 patients require hospital admission, 16,000 of whom have injuries of such significance that care is best undertaken in a burn center. House and structure fires are responsible for >70% of the yearly 5,400 burn-related deaths, of which three fourths result from smoke inhalation or asphyxiation and one fourth are due to burns. However, these fires are responsible for only 4% of burn admissions. Injuries due to contact with flame or ignition of clothing are the most common cause of burn in adults, whereas scald burns are most common in children. The majority of patients sustain burns limited severity and extent (>80% of burns involve <20% of the body surface) that they can be treated on an outpatient basis. There are 250 to 275 patients per million population per year who require hospital admission owing to the extent of their burns or to other complicating factors. Approximately one third of patients who require in-hospital care have a major burn injury—as defined by the American Burn Association on the basis of burn size, causative agent, pre-existing disease, and associated injuries-and should be treated in a tertiary care burn center. Other causes of burns are fire, electricity, chemical substances and even sunshine. In The Netherlands, around 200 people die of their burn incident each year, mostly at the place of the accident. The case fatality rate of scald injury is low; instead most deaths occur in residential fires, commonly caused by careless smoking, by arson or by defective or inappropriately used heating devices. The skin consists of two morphologically different layers that are derived from two different germ layers. The more superficial layer, the epidermis, is a specialized epithelial tissue derived from surface ectoderm. The deeper and thicker layer, the dermis, is composed of vascular dense connective tissue derived from mesenchyme.

In recent years, the concept of the epidermis has gradually been changing from that of an innocent bystander, which, in its strictest sense, protects the body from the loss of fluids and electrolytes, and the penetration of harmful substances, into that of an active participant in several important processes. The dermis is situated between the epidermis and the subcutaneous fat. It supports the epidermis structurally and nutritionally. Its thickness varies, being greatest in the palms and soles and the least in the eyelids. With aging, the dermis becomes thinner and loses elasticity. The dermis interdigitates with the epidermis, so that the upward projections of the dermis, the dermal papillae, interlock with downward ridges of the epidermis, the rete ridges. Like all connective tissue, the dermis has three components: cells, fibers and amorphous ground substance. The bulk of the dermis consists of a network of fibers, principally collagen, but also reticulin and elastin, packed in bundles. Those in the papillary dermis being finer than those in the deeper, reticular dermis. The amorphous ground substance of the dermis consists largely of two glycosaminoglycans: hyaluronic acid and dermatan sulfate, with smaller amounts of heparan and chondroitin sulfate. The function of the ground substance is that it binds water, in order to allow nutrients, hormones and waste products to pass through the dermis. It also is a lubricant between the collagen and elastic fiber network during skin movement and it provides bulk, allowing the dermis to act as a shock absorber. The dermis also contains muscles, both smooth and striated, and vessels. Blood vessels are not only necessary for feeding, but also for regulation of the body temperature. Besides that, blood vessels play a role in allowing transendothelial migration of immune cells, by expressing adhesion molecules that bind to receptor molecules on the immune cells. This transmigration process allows immune cells into the tissue to do their surveillance work. Lymphatic vessels, beginning as blind-ended capillaries in the dermal papillae, pass to either the superficial lymphatic plexus in the papillary dermis, or to the deeper horizontal plexuses. They play a role in water homeostasis of the dermal tissue and also in the recirculation of immune cells.

Thermal energy is a manifestation of random molecular kinetic energy. This energy is easily transferred from high energy molecules to those with a lower energy status during contact, for example in living tissues. Both the temperature and the time period for which this temperature is sustained determine the degree of damage to a cell. At temperatures between 40 and 44° C., various enzyme systems begin to malfunction, and early denaturation of protein occurs. Cellular functions become impaired, one of which is the membrane $Na^+$ pump. This results in a high intracellular $Na^+$ concentration and concomitant swelling of the cell. As the temperature increases, damage accumulation outruns the cell's inherent repair mechanisms and leads to eventual necrosis. The production of oxygen free radicals is part of this damage process. These highly reactive molecules are capable of promoting further cell membrane abnormalities, leading to cell death. If the heat source is suddenly withdrawn, damage accumulation will continue until the cooling process brings cells back down to a normal temperature range. Cooling determines the difference between cell survival and cell death.

As the temperature increases, protein coagulation takes place, which causes destruction of the protein architecture. New aberrant bonds are formed, creating macromolecules not similar to the original structures. The cell necrosis is complete, usually beginning at the skin surface, where the heat energy was absorbed most directly, extending downward. This zone is called the zone of coagulation. The zone of stasis lies deeper and peripheral to the zone of coagulation. In this zone the damage is less and most cells are initially viable. However, the blood flow becomes progressively impaired and finally stops. This development of ischemia results in necrosis of the already affected cells. Peripheral to this zone is the zone of hyperemia, which is characterized by minimal cellular injury and prominent vasodilatation with increased blood flow, due to vasoactive mediators that were produced as part of the inflammatory response. Complete cellular recovery usually happens from this zone up only when capillaries will grow back upward.

Burns can be divided into different categories, based on the depth level of the tissue damage. First degree burn injury involves damage only to the epidermis and is rarely clinically significant other than being painful. The involved area is initially erythematosus due to vasodilatation. Eventually desquamation happens, but this is followed by complete scarless healing within 7 days. Second degree burns are partial-thickness by definition and are further categorized into superficial and deep. In superficial injuries, the epidermis is destroyed as well as varying superficial portions of the dermis. These lesions are usually painful. Blistering is often present. Healing generally occurs rapidly and completely through migration to the surface of epithelial stem cells which survive in deeper portions of the hair follicles as well as the sweat and sebaceous glands. Relatively little scarring occurs in a superficial injury, due to the limited inflammatory phase, which is cut short by wound closure (re-epithelialization) occurring within 2 weeks. In deep partial-thickness wounds, most of the dermis is destroyed and only in the deepest parts of the hair follicles, sweat and sebaceous glands few epithelial cells remain. As the epithelial cells have to migrate from the depth, and due to the loss of stem cells, re-epithelialization is greatly retarded in these wounds. Heat kills the superficial nerve endings, so the wound is relatively insensitive. As the deeply situated pressure receptors may survive, pressure sensation can still be present. Blistering is usually absent due to the thicker adherent overlying eschar which prevents the lifting by the edema. Due to the long period wound closure, the inflammatory phase is prolonged, which gives rise to extensive collagen deposition and consequently abundant scar formation. In third degree or full-thickness burns necrosis of the entire thickness of the skin occurs. As there are no epithelial appendages left, healing can only occur by re-epithelialization from the wound edges, or, in case of small wounds, by contraction of the wound edges. So third degree wounds are routinely treated with excision and skin grafting, serving as a source of new stem cells. As no nerve endings are left, this type of wound is insensitive.

Infection, the risk of which is proportional to the extent of injury, continues to be the predominant determinant of outcome in thermally injured patients despite improvements in overall care in general and wound care in particular. In particular, as a manifestation of the systemic immunosuppressive effects of burn injury, infection at other sites, predominantly in the lungs, remains the most typical cause of morbidity and death in these severely injured patients. Burn patients with or without inhalation injury commonly exhibit a clinical picture produced by systemic inflammation. The phrase "systemic" inflammatory response syndrome (SIRS)" has been introduced to designate the signs and symptoms of patients suffering from such a condition. SIRS has a continuum of severity ranging from the presence of tachycardia, tachypnea, fever and leukocytosis, to refractory hypotension and, in its most severe form, shock and multiple organ system dysfunction.

In thermally injured patients, the most common cause of SIRS is the burn itself. Sepsis, SIRS with the presence of infection or bacteremia, is also a common occurrence. Pathological alterations of metabolic, cardiovascular, gastrointestinal, and coagulation systems occur as a result of the hyperactive immune system. Paradoxically, a state of immunosuppression often follows or co-exists with SIRS. The counter anti-inflammatory response syndrome (CARS) appears to be an adaptive mechanism designed to limit the injurious effects of systemic inflammation. However, this response may also render the host more susceptible to systemic infection due to impaired antimicrobial immunity. Both cellular and humoral mechanisms are involved in these disease processes and have been extensively studied in various burn and sepsis models. The phrase systemic inflammatory response syndrome (SIRS) was recommended by the American College of Chest Physicians/Society for Critical Care Medicine (ACCP/SCCM) consensus conference in 1992 to describe a systemic inflammatory process, independent of its cause. The proposal was based on clinical and experimental results indicating that a variety of conditions, both infectious and noninfectious (i.e. burns, ischemia-reperfusion injury, multiple trauma, pancreatitis), induce a similar host response. Two or more of the following conditions must be fulfilled for the diagnosis of SIRS to be made:

Body temperature >38° C. or <36° C.;

Heart rate >90 beats/min.;

Respiratory rate >20/min or $Paco_2$<32 mmHg;

Leukocyte count >12,000/µl, <4000/µL, or >10% immature (band) forms

All of these pathophysiological changes must occur as an acute alteration from baseline in the absence of other known causes for them such as chemotherapy-induced neutropenia and leukopenia.

The control of invasive burn wound infection through the use of effective topical chemotherapy, prompt surgical excision, and timely closure of the burn wound has resulted in unsurpassed survival rates. Even so, infection remains the most common cause of death in these severely injured patients.

Changes in wound care over the past thirty years, including the use of effective topical antimicrobial chemotherapy and excision of the burned tissue to achieve timely closure of the burn wound, have significantly reduced the occurrence of invasive burn wound infection and its related morbidity and mortality. Regular collection of cultures from patients permits early identification of the causative pathogens of those infections that do arise. Moreover, infection control procedures, including strict enforcement of patient and staff hygiene and use of patient isolation methods, have been effective in controlling the spread of resistant organisms and eliminating them from the burn centre. These advances and the improvements in the general care of critically ill burn patients have resulted in markedly improved survival rates.

Provided is a method for modulating or treating a burn injury in a subject believed to be in need thereof, the method comprising providing the subject with a signaling molecule comprising a gene-regulatory peptide or functional analogue thereof wherein the signaling molecule is administered in an amount sufficient to modulate the burn injury.

The signal molecule is preferably a short peptide, preferably of at most 30 amino acids long, or a functional analogue or derivative thereof. In a very preferred embodiment, the peptide is an oligopeptide of from about 3 to about 15 amino acids long, preferably 4 to 12, more preferably 4 to 9, most preferably 4 to 6 amino acids long, or a functional analogue or derivative thereof. Such a signaling molecule can be longer, for example by extending it (N- and/or C-terminally), with more amino acids or other side groups, which can, for example, be (enzymatically) cleaved off when the molecule enters the place of final destination.

In particular, a method is provided wherein the signaling molecule modulates translocation and/or activity of a gene transcription factor. It is particularly useful when the gene transcription factor comprises an NF-kappaB/Rel protein or an AP-1 protein. Burn injuries generally induce increased expression of inflammatory cytokines due to activation of NF-κB and AP-1, and in a preferred embodiment provided is a method wherein translocation and/or activity of the NF-kappaB/Rel protein is inhibited. In one embodiment, the peptide is selected from the group of peptides LQG, AQG, LQGV (SEQ ID NO: 1 of the hereby incorporated accompanying SEQUENCE LISTING), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LQGVLPALPQVVC (SEQ ID NO:17), LPGCPRGVNPVVS (SEQ ID NO:18), LPGC (SEQ ID NO:19), MTRV (SEQ ID NO:20), MTR, VVC. Burn injury induces increased expression of inflammatory cytokines due to activation of NF-κB and AP-1. Inflammatory cytokines can be expressed by epithelium, perivascular cells and adherent or transmigrating leukocytes, inducing numerous pro-inflammatory and procoagulant effects. Together these effects predispose to inflammation, thrombosis and hemorrhage. Of clinical and medical interest and value, provided is the opportunity to selectively control NFκB-dependent gene expression in tissues and organs in a living subject, preferably in a primate, allowing up regulating essentially anti-inflammatory responses such as IL-10, and down regulating essentially pro-inflammatory responses such as mediated by TNF-alpha, nitric oxide (NO), IL-5, IL-1beta.

Provided is the use of a NFκB regulating peptide or derivative thereof for the production of a pharmaceutical composition for the treatment of a burn injury, preferably in a primate, and provides a method of treatment of a burn injury, notably in a primate. It is preferred when the treatment comprises administering to the subject a pharmaceutical composition comprising an NFkappaB down-regulating peptide or functional analogue thereof. Examples of useful NFkappaB down-regulating peptides are VLPALPQVVC (SEQ ID NO:21), LQGVLPALPQ (SEQ ID NO:22), LQG, LQGV (SEQ ID NO:1), GVLPALPQ (SEQ ID NO:23), VLPALP (SEQ ID NO:4), VVC, MTR and circular LQGVLPALPQVVC (SEQ ID NO:17). More down-regulating peptides and functional analogues can be found using the methods as provided herein. Most prominent among NFkappaB down-regulating peptides are VLPALPQVVC (SEQ ID NO:21), LQGVLPALPQ (SEQ ID NO:22), LQG, LQGV (SEQ ID NO:1), and VLPALP (SEQ ID NO:4). These are also capable of reducing production of NO by a cell. It is herein also provided to use a composition that comprises at least two oligopeptides or functional analogues thereof, each capable of down-regulating NFkappaB, and thereby reducing production of NO and/or TNF-alpha by a cell, in particular wherein the at least two oligopeptides are selected from the group LQGV (SEQ ID NO:1), AQGV (SEQ ID NO:2), and VLPALP (SEQ ID NO:4), for the treatment of a burn injury, and, moreover to treat the systemic inflammatory response often seen in severe burn patients.

Thus provided is the use of a such signaling molecule comprising a NF-kappaB down-regulating peptide or functional analogue thereof for the production of a pharmaceutical composition for the treatment of a systemic inflammatory response syndrome occurring after a burn injury of a subject, in particular wherein translocation and/or activity of the NF-kappaB/Rel protein is inhibited, resulting in keeping the cascade of cytokine reactions that in general lead to SIRS at bay.

In general, when treating burns patients, two, often conflicting needs of the patient need be met. For one, the treatment of the affected, and locally seriously inflamed, skin deserves particular attention; on the other hand, the patient may also suffer from the consequences of a more systemic inflammatory response.

Thermal injury initiates a deleterious pathophysiological response in every organ system, with the extent and duration of organ dysfunction proportionate to the size of the burn. Direct cellular damage is manifested by coagulation necrosis, with the depth of tissue destruction determined by the duration of contact and the temperature to which the tissue is exposed. Following burn, the normal skin barrier to microbial penetration is lost, and the moist, protein-rich avascular eschar of the burn wound provides an excellent culture medium for microorganisms, which infect the burn injury. Although the body logically responds to these infections by eliciting a (local) inflammation, provided is use of a signaling molecule comprising a NF-kappaB down-regulating peptide or functional analogue thereof for the production of a pharmaceutical composition for the topical treatment of a burn wound in a subject, to actually counter the inflammation and prevent systemic responses and overly active scar tissue formation.

Also provided is a pharmaceutical composition comprising an NF-kappaB down-regulating peptide or functional analogue thereof and a bactericidal or bacteriostatic compound or a compound comprising silver. Wound management will vary according to the depth of the burn. The true depth of the burn will become more obvious with time and therefore the wound must be reassessed to ensure that wound management is appropriate. Systemic, and even topical, antibiotics are not to be used prophylactically, and are in general only appropriate when demonstrated infection is present, however, is in particular useful that translocation and/or activity of the NF-kappaB/Rel protein is inhibited to counter the local cytokine cascade leading to an inflammation by the inclusion of one or more of the NFkappaB down-regulating peptides or functional analogues thereof as identified herein, and at that time it is even more useful that the pharmaceutical composition for topical use is also provided with antibacterial compounds, preferably compounds that comprise silver, such as a antibacterial cream or ointment comprising micronized silver sulfadiazine and an NFkappaB down-regulating peptide. Thus, provided is a method to treat a burn injury of a subject wherein the subject is provided with a topical agent directed against a bacterial infection such as a bacteriostatic or bactericidal compound such as tetracycline or a sulfa compound wherein the topical agent also comprises a NFkappaB down-regulating peptide at a concentration of for example 1 to 1,000 microg/g, preferably 50-300 microg/g. Typical other substances found in such a cream or ointment are 10 mg/gram of micronized silver sulfadiazine and a lege artis cream vehicle composed of white petrolatum, stearyl alcohol, isopropyl myristate, sorbitan monooleate, polyoxyl 40 stearate, propylene glycol, and water. Another anti-inflammatory and anti-infective cream for topical administration to burn wounds as herein provided comprises one or more of NFkappaB down-regulating peptides VLPALPQVVC (SEQ ID NO:21), LQGVLPALPQ (SEQ ID NO:22), LQG, LQGV (SEQ ID NO:1), GVLPALPQ (SEQ ID NO:22), VLPALP (SEQ ID NO:4), VVC, MTR at a concentration of, for example, 50-300 micrograms/gram and contains, per gram, mafenide acetate equivalent to 85 mg of the base. The cream vehicle for example consists of cetyl alcohol, stearyl alcohol, cetyl esters wax, polyoxyl 40 stearate, polyoxyl 8 stearate, glycerin, and water, with methylparaben, propylparaben, sodium metabisulfite, and edetate disodium as preservatives may be added. While destruction of the mechanical barrier of the skin contributes to the increased susceptibility to infection, post-burn alterations in immune function may also be of significant importance. Every component of the humoral and cellular limbs of the immune system appears to be affected after thermal injury; the magnitude and duration of dysfunction are proportional to the extent of injury.

Wound healing is the consequence of a continuous sequence of signals and responses in which epithelial, vascular, hemopoietic and connective tissue cells come together outside their usual domains, interact, repair the damage and having done so turn back to their normal functions. The purpose of wound healing is to restore the functions of the skin, such as protection of the body against harmful environmental entities, prevention of entry of microorganisms and loss of plasma, the regulation of body temperature, the processing and interpretation of environmental information through the neurosensory system and a social-interactive function. Vertical cutaneous injuries, such as surgical incisions which have a minimal loss of tissue, will essentially heal through the formation of a blood clot, rapid epithelialization, and fibroblast proliferation. Progressive collagenization and increased strength, which reach normal levels within weeks, will complete the healing process and leave discrete scarring, in most cases.

On the other hand, cutaneous wounds with a predominant horizontal loss of tissue, like burn injuries, exhibit a healing that proceeds through a series of complex, biological mechanisms according to the extent and level of the involved structures. In particular, the destruction of the normal capillary system that is involved to the blood supply of the skin creates additional problems. A burn wound that suffers from decreased blood supply becomes ischemic, hypoxic, and highly edematous. For the various stages in the burn wound healing process use of a signaling molecule of the invention for the preparation of a pharmaceutical composition for modulation of vascularization or angiogenesis in wound repair, in particular of burns, is herein provided.

Not only may one treat topical and systemically with NFkappaB down-regulating peptides to find the best balance between a local inflammatory response while keeping systemic inflammation at bay; according to the instant disclosure, one may also increase vasculogenesis by the topical application of modulatory peptides such LQG, VVC and MTRV (SEQ ID NO:20), and in particular LQGV (SEQ ID NO:1), which promote angiogenesis, especially in topical applications. Such angiogenesis-promoting compositions may be composed of 200-600 microg/ml of for example LQGV (SEQ ID NO:1) in a gel vehicle that is for example composed of an oil-in-water emulsion base of glycerin, cetyl alcohol, stearic acid, glyceryl monostearate, mineral oil, polyoxyl 40 stearate, and purified water. These can also be included in cream or ointment compositions as described above in the absence of sufficient angiogenesis, burn wound healing follows a much slower course compared with the healing of other types of wounds.

The wound healing response can be divided into three distinct, but overlapping phases: 1) hemostasis and inflammation; 2) dermal and epidermal proliferation; and 3) maturation and remodeling. The first response after disruption of tissue integrity is to control the damage produced to the vascular system. A hemorrhage means immediate danger to the body, which reacts with prompt vasoconstriction, platelet aggregation and activation of the coagulation system. The initial response to deep burns involves a transient 5- to 10-minute period of intense vasoconstriction that aids in hemostasis. This is followed by active vasodilation that usually becomes most pronounced approximately 20 minutes after the injury and is accompanied by an increased capillary permeability. Histamine is believed to be a key chemical mediator responsible for the vasodilation and the danger in vascular permeability. Shortly after burning, platelet adhesion occurs at the site of the burn. Platelets function to initiate the formation of a clot that helps to achieve hemostasis. The contact between the extracellular matrix and platelets, as well as the presence of thrombin and fibronectin, results in the release of growth factors and vasoactive substances such as platelet-derived growth factor (PDGF), transforming growth factor-beta (TGF-beta), fibroblast growth factor (FGF), epidermal growth factor (EGF), bradykinin, prostaglandins, prostacyclines, thromboxane, histamine and serotonin. Platelet degranulation also initiates the complement cascade with the formation of C3a and C5a, which are potent anaphylatoxins promoting the release of histamine by basophils and mast cells. When angiogenesis is promoted in a method as provided herein these series of events are accompanied by improved blood supply from regenerating tissue which ultimately leads to less complicated wound healing. Also, granulocytes, in a rapid response to signaling by platelets and also through factors produced by the activation of the complement system, form the first line of defense against local bacterial contamination. In the absences of bacterial contamination, the granulocyte has been claimed to be non-essential to the wound healing process. Usually within 24-72 hours, the granulocytes are gradually replaced by monocytes that acquire the characteristics of tissue macrophages and become central coordinators of the inflammatory and repair process. Macrophages not only help to clean the wounded area of undesirable debris and bacteria, but they also promote the build up of the new connective tissue. Through growth factors and cytokines like TGF-beta, PDGF and EGF, tumor necrosis factor-alpha (TNF-alpha), interleukin-1 (IL-1) and interferon-gamma (IFN-gamma), through enzymes like collagenase and arginase, and through prostaglandins, they regulate the matrix synthesis by affecting either fibroblast chemotaxis or proliferation, or collagen synthesis. Macrophages also play a role in mediating angiogenesis and in the recruitment and activation of other immune cells. By timely inclusion the use of NFkappaB down-regulating peptides in the treatment of burn injury, overly strong collagen matrix development can be modulated such that kyloid scars due to ridge formation are less well likely to develop.

Furthermore, it has been demonstrated that activated T lymphocytes, following the influx of granulocytes and macrophages, enter a wound area by day 4 or 5 and become important modulators of the healing process. An intact T-cell immune system is essential, at least indirectly, for a normal healing outcome. Other cells, like mast cells, and their major protease, chymase, also play a role in the wound healing process by promoting capillary outgrowth and collagen formation. Again, these processes react well on treatment with NFkappaB down-regulating peptides. It has also been suggested that dermal dendritic cells participate in wound repair by initiating the inflammatory response and by stimulating epithelial proliferation and restoration of epithelial architecture. However, part of their function is now taken over by providing the healing wound with regular treatments with a NFkappaB down regulating peptide, supplemented by treatment with a angiogenesis modulating peptide.

The crucial pathophysiologic event that precipitates systemic inflammation is tissue damage. This can occur both as a result of the direct injury to tissues from mechanical or thermal trauma as well as cellular injury induced by mediators of ischemia-reperfusion injury such as oxygen free radicals. Injury results in the acute release of proinflammatory cytokines. If injury is severe, such as in extensive thermal injury, a profound release of cytokines occurs, resulting in the induction of a systemic inflammatory reaction, of which disseminated intravascular coagulation is often seen at on or more stages of the healing process. The ability of the host to adapt to this systemic inflammatory response is dependent on the magnitude of the response, the duration of the response, and the adaptive capacity of the host. Factors that have been implicated in prolongation of SIRS include under-resuscitation in the acute phase following thermal injury, persistent or intermittent infection, ongoing tissue necrosis, and translocation of endotoxin across the bowel.

In certain embodiments, provided are method and means to treat the systemic reaction to burns injuries by providing a subject believed to be in need thereof with a pharmaceutical composition comprising a NF-kappaB down-regulating peptide or functional analogue thereof and an agent directed against disseminated intravascular coagulation. Such an agent may for example be a composition comprising heparin, however, in a preferred embodiment, provided is treatment with a hypotonic pharmaceutical composition comprising a NF-kappaB down-regulating peptide or functional analogue thereof. Such treatment may for example comprise infusions with Ringer's lactate for the first 24 hours, the Ringer's lactate provided with, preferably, 1-1000 mg/l NFkappaB regulating peptide such as VLPALPQVVC (SEQ ID NO:21), LQGVLPALPQ (SEQ ID NO:22), LQG, LQGV (SEQ ID NO:1), or VLPALP (SEQ ID NO:4), or mixtures of two or more of such peptides.

At this stage, it is important to keep the volume up, and, if needed, provide the peptide or functional analogue thereof in even further hypotonic solutions, such as 0.3 to 0.6% saline. NFkappaB regulating peptide can be given in the same infusion, the peptide (or analogue) concentration preferably being from about 1 to about 1000 mg/l, but the peptide can also been given in a bolus injection. Doses of 1 to 5 mg/kg body weight, for example every eight hours in a bolus injection or per infusionem until the patient stabilizes, are recommended. For example in cases where large affected areas are expected or diagnosed, it is preferred to monitor cytokine profiles, such as TNF-alpha or IL-10 levels, arachidonic acid metabolites an NO in the plasma of the treated patient, and to stop treatment when these levels are considered within normal boundaries. In another embodiment, it is herein provided to modulate a burn injury in a subject comprising providing the subject with a signaling molecule comprising a gene-regulatory peptide or functional analogue thereof wherein the subject is also provided with an agent directed against disseminated intravascular coagulation, in particular wherein the agent comprises Activated Protein C activity. Such an agent to modulate disseminated intravascular coagulation (DIC) comprises preferably (recombinant) human Activated Protein C. It is preferably given to the patient per infusionem, whereby NFkappaB regulating peptide can be given in the same infusion, the peptide (or analogue) concentration preferably being from about 1 to about 1000 mg/l, but the peptide can also been given in a bolus injection. Doses of 1 to 5 mg/kg body weight, for example every eight hours in a bolus injection or per infusionem until the patient stabilizes, are recommended.

DETAILED DESCRIPTION OF THE INVENTION

Provided is a method for modulating a burn injury in a subject comprising providing the subject with a signaling molecule comprising a gene-regulatory peptide or functional analogue thereof, in particular wherein the signaling molecule down-regulates translocation and/or activity of a gene transcription factor, especially wherein the gene transcription factor comprises an NF-kappaB/Rel protein, particularly wherein translocation and/or activity of the NF-kappaB/Rel protein is inhibited. Such peptides may be selected from peptides having NFkappaB down- or up-regulating activity in LPS stimulated RAW264.7 cells. In a preferred embodiment, provided is a method for modulating a burn injury in a subject comprising providing the subject with a gene-regulatory peptide selected from the group of as LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:13), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LPGC (SEQ ID NO:19), MTRV (SEQ ID NO:20), MTR, and VVC. More gene-regulating peptides and functional analogues can be found in an assay or bioassay, such as a NFkappaB translocation assay as provided herein, and a by testing peptides for NFkappaB down- or up-regulating activity in LPS-stimulated or unstimulated RAW264.7 cells. For anti-inflammatory treatment, it is preferred that the peptide is selected from the group of peptides having NFkappaB down-regulating activity in LPS stimulated RAW264.7 cells, especially when the subject is at risk to experience a "systemic inflammatory response syndrome" ("SIRS") occurring after a burn injury. In certain embodiments, a method according to the invention is provided wherein the peptide is selected from the group of LAGV (SEQ ID NO:10), AQGV (SEQ ID NO:2), VLPALPQ (SEQ ID NO:13), and LQGV (SEQ ID NO:1) for use in the treatment of skin inflammations seen with burns. It is particularly preferred to use a peptide is selected from the group of LAGV (SEQ ID NO:10), AQGV (SEQ ID NO:2), and LQGV (SEQ ID NO:1) in cases of SIRS with burns.

Furthermore, a method is provided wherein the subject is also provided with an agent directed against disseminated intravascular coagulation, such as wherein the agent comprises Activated Protein C activity.

For the treatment of burns a various pharmaceutical compositions are provided, for example pharmaceutical composition comprising a peptide selected from the group of LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LPGC (SEQ ID NO:19), MTRV (SEQ ID NO:20), MTR, and VVC (preferably LAGV (SEQ ID NO:10), AQGV (SEQ ID NO:2), or LQGV (SEQ ID NO:1)) and an agent directed against disseminated intravascular coagulation. Furthermore, provided is a hypotonic pharmaceutical composition comprising a peptide selected from the group of LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPAPLA (SEQ ID NO:15), GVLPALP (SEQ ID NO:16), LPGC (SEQ ID NO:19), MTRV (SEQ ID NO:20), MTR, and VVC, preferably LAGV (SEQ ID NO:10), AQGV (SEQ ID NO:2), or LQGV (SEQ ID NO:1) are provided in that hypotonic composition. Also, provided is a pharmaceutical composition comprising a peptide selected from the group of LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPAPLA (SEQ ID NO:15), GVLPALP (SEQ ID NO:16), LPGC (SEQ ID NO:19), MTRV (SEQ ID NO:20), MTR, and VVC and a bacteriostatic compound comprising silver, preferably for such mixtures VLPALPQ (SEQ ID NO:13), LAGV (SEQ ID NO:10), AQGV (SEQ ID NO:2), or LQGV (SEQ ID NO:1) are used.

In response to a variety of pathophysiological and developmental signals, the NFkB/Rel family of transcription factors are activated and form different types of hetero- and homodimers among themselves to regulate the expression of target genes containing kappaB-specific binding sites. NF-kB transcription factors are hetero- or homodimers of a family of related proteins characterized by the Rel homology domain. They form two subfamilies, those containing activation domains (p65-RELA, RELB, and c-REL) and those lacking activation domains (p50, p52). The prototypical NFkB is a heterodimer of p65 (RELA) and p50 (NF-kB1). Among the activated NFkB dimers, p50-p65 heterodimers are known to be involved in enhancing the transcription of target genes and p50-p50 homodimers in transcriptional repression. However, p65-p65 homodimers are known for both transcriptional activation and repressive activity against target genes. KappaB DNA binding sites with varied affinities to different NFkappaB dimers have been discovered in the promoters of several eukaryotic genes and the balance between activated NFkB homo- and heterodimers ultimately determines the nature and level of gene expression within the cell. The term "NFkB-regulating peptide" as used herein refers to a peptide or a modification or derivative thereof capable of modulating the activation of members of the NFkB/Rel family of transcription factors. Activation of NFkB can lead to enhanced transcription of target genes. Also, it can lead to transcriptional repression of target genes. NFkB activation can be regulated at multiple levels. For example, the dynamic shuttling of the inactive NFkB dimers between the cytoplasm and nucleus by IkappaB proteins and its termination by phosphorylation and proteasomal degradation, direct phosphorylation, acetylation of NFkB factors, and dynamic reorganization of NFkB subunits among the activated NFkB dimers have all been identified as key regulatory steps in NFkB activation and, consequently, in NFkB-mediated transcription processes. Thus, an NFkB-regulating peptide is capable of modulating the transcription of genes that are under the control of NFkB/Rel family of transcription factors. Modulating comprises the upregulation or the downregulation of transcription. In a preferred embodiment, a peptide according to the invention, or a functional derivative or analogue thereof is used for the production of a pharmaceutical composition. Such peptides are preferably selected from group of peptides having NFkappaB down-regulating activity in LPS stimulated RAW264.7 cells. Examples of useful NFkappaB down-regulating peptides to be included in such a pharmaceutical composition are VLPALPQVVC (SEQ ID NO:21), LQGVLPALPQ (SEQ ID NO:21), LQG, LQGV (SEQ ID NO:1), GVLPALPQ (SEQ ID NO:23), VLPALP (SEQ ID NO:4), VVC, MTR and circular LQGVLPALPQVVC (SEQ ID NO:17). More gene-regulating peptides and functional analogues can be found in a bioassay or assay, such as a NFkappaB translocation assay as provided herein, which can also be used to further identify peptides having NFkappaB up-regulating activity in LPS stimulated RAW264.7 cells. Most prominent among NFkappaB down-regulating peptides are VLPALPQVVC (SEQ ID NO:21), LQGVLPALPQ (SEQ ID NO:21), LQG, LQGV (SEQ ID NO:1), and VLPALP (SEQ ID NO:4). These are also capable of reducing production of NO by a cell. It is herein also provided to use a composition that comprises at least two oligopeptides or functional analogues thereof, each capable of down-regulating NFkappaB, and thereby reducing production of NO and/or TNF-alpha by a cell, in particular wherein the at least two oligopeptides are selected from the group LQGV (SEQ ID NO:1), AQGV (SEQ ID NO:2), and VLPALP (SEQ ID NO:4). Useful NFkappaB up-regulating peptides are VLPALPQ (SEQ ID NO:13), GVLPALP (SEQ ID NO:16), and MTRV (SEQ ID NO:20). As indicated, more gene-regulatory peptides may be found with an appropriate bioassay or assay. A gene-regulatory peptide as used herein is preferably short. Preferably, such a peptide is 3 to 15 amino acids long, more preferably, wherein the lead peptide is 3 to 9 amino acids long, most preferred wherein the lead peptide is 4 to 6 amino acids long, and capable of modulating the expression of a gene, such as a cytokine, in a cell. In a preferred embodiment, a peptide is a signaling molecule that is capable of traversing the plasma membrane of a cell or, in other words, a peptide that is membrane-permeable.

Functional derivative or analogue herein relates to the signaling molecular effect or activity as for example can be measured by measuring nuclear translocation of a relevant transcription factor, such as NF-kappaB in an NF-kappaB assay, or AP-1 in an AP-1 assay, or by another method as provided herein. Fragments can be somewhat (i.e. 1 or 2 amino acids) smaller or larger on one or both sides, while still providing functional activity. Such a bioassay comprises an assay for obtaining information about the capacity or tendency of a peptide, or a modification thereof, to regulate expression of a gene. A scan with for example a 15-mer, or a 12-mer, or a 9-mer, or a 8-mer, or a 7-mer, or a 6-mer, or a 5-mer, or a 4-mer or a 3-mer peptides can yield valuable information on the linear stretch of amino acids that form an interaction site and allows identification of gene-regulatory peptides that have the capacity or tendency to regulate gene expression. Gene-regulatory peptides can be modified to modulate their capacity or tendency to regulate gene expression, which can be easily assayed in an in vitro bioassay such as a reporter assay. For example, some amino acid at some position can be replaced with another amino acid of similar or different properties. Alanine (Ala)-replacement scanning, involving a systematic replacement of each amino acid by an Ala residue, is a suitable approach to modify the amino acid composition of a gene-regulatory peptide when in a search for a signaling molecule capable of modulating gene expression. Of course, such replacement scanning or mapping can be undertaken with amino acids other than Ala as well, for example with D-amino acids. In one embodiment, a peptide derived from a naturally occurring polypeptide is identified as being capable of modulating gene expression of a gene in a cell. Subsequently, various synthetic Ala-mutants of this gene-regulatory peptide are produced. These Ala-mutants are screened for their enhanced or improved capacity to regulate expression of a gene compared to gene-regulatory polypeptide.

Furthermore, a gene-regulatory peptide, or a modification or analogue thereof, can be chemically synthesised using D- and/or L-stereoisomers. For example, a gene-regulatory peptide that is a retro-inverso of an oligopeptide of natural origin is produced. The concept of polypeptide retro-inversion (assemblage of a natural L-amino acid-containing parent sequence in reverse order using D-amino acids) has been applied successfully to synthetic peptides. Retro-inverso modification of peptide bonds has evolved into a widely used peptidomimetic approach for the design of novel bioactive molecules which has been applied to many families of biologically active peptide. The sequence, amino acid composition and length of a peptide will influence whether correct assembly and purification are feasible. These factors also determine the solubility of the final product. The purity of a crude peptide typically decreases as the length increases. The yield of peptide for sequences less than 15 residues is usually satisfactory, and such peptides can typically be made without difficulty. The overall amino acid composition of a peptide is an important design variable. A peptide's solubility is strongly influenced by composition. Peptides with a high content of hydrophobic residues, such as Leu, Val, Ile, Met, Phe and Trp, will either have limited solubility in aqueous solution or be completely insoluble. Under these conditions, it can be difficult to use the peptide in experiments, and it may be difficult to purify the peptide if necessary. To achieve a good solubility, it is advisable to keep the hydrophobic amino acid content below 50% and to make sure that there is at least one charged residue for every five amino acids. At physiological pH Asp, Glu, Lys, and Arg all have charged side chains. A single conservative replacement, such as replacing Ala with Gly, or adding a set of polar residues to the N- or C-terminus, may also improve solubility. Peptides containing multiple Cys, Met, or Trp residues can also be difficult to obtain in high purity partly because these residues are susceptible to oxidation and/or side reactions. If possible, one should choose sequences to minimize these residues. Alternatively, conservative replacements can be made for some residues. For instance, Norleucine can be used as a replacement for Met, and Ser is sometimes used as a less reactive replacement for Cys. If a number of sequential or overlapping peptides from a protein sequence are to be made, making a change in the starting point of each peptide may create a better balance between hydrophilic and hydrophobic residues. A change in the number of Cys, Met, and Trp residues contained in individual peptides may produce a similar effect. In another embodiment of the invention, a gene-regulatory peptide capable of modulating gene expression is a chemically modified peptide. A peptide modification includes phosphorylation (e.g., on a Tyr, Ser or Thr residue), N-terminal acetylation, C-terminal amidation, C-terminal hydrazide, C-terminal methyl ester, fatty acid attachment, sulfonation (tyrosine), N-terminal dansylation, N-terminal succinylation, tripalmitoyl-S-Glyceryl Cysteine (PAM3 Cys-OH) as well as farnesylation of a Cys residue. Systematic chemical modification of a gene-regulatory peptide can for example be performed in the process of gene-regulatory peptide optimization.

Synthetic peptides can be obtained using various procedures known in the art. These include solid phase peptide synthesis (SPPS) and solution phase organic synthesis (SPOS) technologies. SPPS is a quick and easy approach to synthesize peptides and small proteins. The C-terminal amino acid is typically attached to a cross-linked polystyrene resin via an acid labile bond with a linker molecule. This resin is insoluble in the solvents used for synthesis, making it relatively simple and fast to wash away excess reagents and by-products.

U.S. Pat. No. 5,380,668 to Herron (Jan. 10, 1995), the contents of the entirety of which are incorporated by this reference, discloses, among other things, various compounds having the antigenic binding activity of hCG. Herron further discloses means and methods for making oligopeptides.

The compounds according to the general formula may be prepared in a manner conventional for such compounds. To that end, suitably N alpha protected (and side-chain protected if reactive side-chains are present) amino acid derivatives or peptides are activated and coupled to suitably carboxyl protected amino acid or peptide derivatives either in solution or on a solid support. Protection of the alpha-amino functions generally takes place by urethane functions such as the acid-labile tertiary-butyloxycarbonyl group ("Boc"), benzyloxycarbonyl ("Z") group and substituted analogs or the base-labile 9-fluoremyl-methyloxycarbonyl ("Fmoc") group. The Z group can also be removed by catalytic hydrogenation. Other suitable protecting groups include the Nps, Bmv, Bpoc, Aloc, MSC, etc. A good overview of amino protecting groups is given in *The poetides, Analysis, Synthesis, Biology*, Vol. 3 E. Gross and J. Meienhofer, eds. (Academic Press, New York, 1981). Protection of carboxyl groups can take place by ester formation, for example, base-labile esters like methyl or ethyl, acid labile esters like tert. butyl or, substituted, benzyl esters or hydrogenolytically. Protection of side-chain functions like those of lysine and glutamic or aspartic acid can take place using the aforementioned groups. Protection of thiol, and although not always required, of guanidino, alcohol and imidazole groups can take place using a variety of reagents such as those described in The Peptides, Analysis, Synthesis, Biology, id. or in Pure and Applied Chemistry, 59(3), 331-344 (1987). Activation of the carboxyl group of the suitably protected amino acids or peptides can take place by the azide, mixed anhydride, active ester, or carbodiimide method especially with the addition of catalytic and racemization-suppressing compounds like 1-N-N-hydroxybenzotriazole, N-hydroxysuccinimide, 3-hydroxy-4-oxo-3,4-dihydro-1,2,3,-benzotria-zine, N-hydroxy-5 norbornene-2,3-dicar-boxyimide. Also the anhydrides of phosphorus based acids can be used. See, e.g., The Peptides, Analysis, Synthesis, Biology, supra and Pure and Applied Chemistry, 59(3), 331-344 (1987).

It is also possible to prepare the compounds by the solid phase method of Merrifield. Different solid supports and different strategies are known, see, e.g., Barany and Merrifield in The Peptides, Analysis, Synthesis, Biology, Vol. 2, E. Gross and J. Meienhofer, eds. (Acad. Press, New York, 1980), Kneib-Cordonier and Mullen Int. J. Peptide Protein Res., 30, 705-739 (1987) and Fields and Noble Int. J. Peptide Protein Res., 35, 161-214 (1990). The synthesis of compounds in which a peptide bond is replaced by an isostere, can, in general, be performed using the previously described protecting groups and activation procedures. Procedures to synthesize the modified isosteres are described in the literature, for instance, for the —$CH_2$—NH-isostere and for the —CO—$CH_2$-isostere.

Removal of the protecting groups, and, in the case of solid phase peptide synthesis, the cleavage from the solid support, can take place in different ways, depending on the nature of those protecting groups and the type of linker to the solid support. Usually deprotection takes place under acidic conditions and in the presence of scavengers. See, e.g., volumes 3, 5 and 9 of the series on *The Peptides Analysis, Synthesis, Biology*, supra.

Another possibility is the application of enzymes in synthesis of such compounds; for reviews see, e.g., H. D. Jakubke in The Peptides, Analysis, Synthesis, Biology, Vol. 9, S. Udenfriend and J. Meienhofer, eds. (Acad. Press, New York, 1987).

Although possibly not desirable from an economic point of view, oligopeptides according to the invention could also be made according to recombinant DNA methods. Such methods involve the preparation of the desired oligopeptide thereof by means of expressing recombinant polynucleotide sequence that codes for one or more of the oligopeptides in question in a suitable microorganism as host. Generally the process involves introducing into a cloning vehicle (e.g., a plasmid, phage DNA, or other DNA sequence able to replicate in a host cell) a DNA sequence coding for the particular oligopeptide or oligopeptides, introducing the cloning vehicle into a suitable eucaryotic or prokaryotic host cell, and culturing the host cell thus transformed. When a eucaryotic host cell is used, the compound may include a glycoprotein portion.

As used herein, a "functional analogue" or "derivative" of a peptide includes an amino acid sequence, or other sequence monomers, which has been altered such that the functional properties of the sequence are essentially the same in kind, not necessarily in amount. An analogue or derivative can be provided in many ways, for instance, through "conservative amino acid substitution." Also peptidomimetic compounds can be designed that functionally or structurally resemble the original peptide taken as the starting point but that are for example composed of non-naturally occurring amino acids or polyamides. With "conservative amino acid substitution," one amino acid residue is substituted with another residue with generally similar properties (size, hydrophobicity), such that the overall functioning is likely not to be seriously affected. However, it is often much more desirable to improve a specific function. A derivative can also be provided by systematically improving at least one desired property of an amino acid sequence. This can, for instance, be done by an Ala-scan and/or replacement net mapping method. With these methods, many different peptides are generated, based on an original amino acid sequence but each containing a substitution of at least one amino acid residue. The amino acid residue may either be replaced by alanine (Ala-scan) or by any other amino acid residue (replacement net mapping). This way, many positional variants of the original amino acid sequence are synthesized. Every positional variant is screened for a specific activity. The generated data are used to design improved peptide derivatives of a certain amino acid sequence.

A derivative or analogue can also be, for instance, generated by substitution of an L-amino acid residue with a D-amino acid residue. This substitution, leading to a peptide that does not naturally occur in nature, can improve a property of an amino acid sequence. It is, for example, useful to provide a peptide sequence of known activity of all D-amino acids in retro inversion format, thereby allowing for retained activity and increased half-life values. By generating many positional variants of an original amino acid sequence and screening for a specific activity, improved peptide derivatives comprising such D-amino acids can be designed with further improved characteristics.

A person skilled in the art is well able to generate analogous compounds of an amino acid sequence. This can, for instance, be done through screening of a peptide library. Such an analogue has essentially the same functional properties of the sequence in kind, not necessarily in amount. Also, peptides or analogues can be circularized, for example, by providing them with (terminal) cysteines, dimerized or multimerized, for example, by linkage to lysine or cysteine or other compounds with side-chains that allow linkage or multimerization, brought in tandem- or repeat-configuration, conjugated or otherwise linked to carriers known in the art, if only by a labile link that allows dissociation.

As used herein, an oligopeptide also includes, for example, an acceptable salt, base, or ester of the oligopeptide or a labeled oligopeptide. As used herein, "acceptable salt" refers to salts that retain the desired activity of the oligopeptide or equivalent compound, but preferably do not detrimentally affect the activity of the oligopeptide or other component of a system in which uses the oligopeptide. Examples of such salts are acid addition salts formed with inorganic acids, for example, hydrochloric acid, hydrobromic acid, sulfuric acid, phosphoric acid, nitric acid, and the like. Salts may also be formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, and the like. Salts may be formed with polyvalent metal cations such as zinc, calcium, bismuth, barium, magnesium, aluminum, copper, cobalt, nickel and the like or with an organic cation formed from N,N'-dibenzylethylenediamine or ethylenediamine, or combinations thereof (e.g., a zinc tannate salt).

The oligopeptide, or its modification or derivative, can be administered as the entity, as such, or as a pharmaceutically acceptable acid- or base addition salt, formed by reaction with an inorganic acid (such as hydrochloric acid, hydrobromic acid, perchloric acid, nitric acid, thiocyanic acid, sulfuric acid, and phosphoric acid); or with an organic acid (such as formic acid, acetic acid, propionic acid, glycolic acid, lactic acid, pyruvic acid, oxalic acid, malonic acid, succinic acid, maleic acid, and fumaric acid); or by reaction with an inorganic base (such as sodium hydroxide, ammonium hydroxide, potassium hydroxide); or with an organic base (such as mono-, di-, trialkyl and aryl amines and substituted ethanolamines). A selected peptide and any of the derived entities may also be conjugated to sugars, lipids, other polypeptides, nucleic acids and PNA; and function in-situ as a conjugate or be released locally after reaching a targeted tissue or organ.

A pharmaceutical composition for use herein may be administered to the subject parenterally or orally. Such a pharmaceutical composition may consist essentially of (or consist of) oligopeptide and PBS. It is preferred that the oligopeptide is of synthetic origin. Suitable treatment, for example, entails administering the oligopeptide (or salt or ester) in the pharmaceutical composition to the patient intravenously in an amount of from about 0.0001 to about 35 mg/kg body mass of the subject. It may be useful that the pharmaceutical composition consists essentially of from one to three different oligopeptides.

The peptides as mentioned in this document such as LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLAPALPA (SEQ ID NO:15), GVLPALP (SEQ ID NO:16), VVCNYRDVRFE-SIRLPGCPRGVNPVVSYAVALSCQCAL (SEQ ID NO:24), RPRCRPINATLAVEKEGCPVCITVNTTI-CAGYCPT (SEQ ID NO:25), SKAPPPSLPSPSRLPGPS (SEQ ID NO:26), LQGVLPALPQVVC (SEQ ID NO:17), SIRLPGCPRGVNPVVS (SEQ ID NO:27), LPGCPRGVN-PVVS (SEQ ID NO:18), LPGC (SEQ ID NO:19), MTRV (SEQ ID NO:20), MTR, and VVC were prepared by solid-phase synthesis using the fluorenylmethoxycarbonyl (Fmoc)/tert-butyl-based methodology with 2-chlorotrityl chloride resin as the solid support. The side-chain of glutamine was protected with a trityl function. The peptides were synthesized manually. Each coupling consisted of the following steps: (i) removal of the alpha-amino Fmoc-protection by piperidine in dimethylformamide (DMF), (ii) coupling of the Fmoc amino acid (3 eq) with diisopropylcarbodiimide (DIC)/1-hydroxybenzotriazole (HOBt) in DMF/N-methylformamide (NMP) and (iii) capping of the remaining amino functions with acetic anhydride/diisopropylethylamine (DIEA) in DMF/NMP. Upon completion of the synthesis, the peptide resin was treated with a mixture of trifluoroacetic acid (TFA)/H$_2$O/triisopropylsilane (TIS) 95:2.5:2.5. After 30 minutes TIS was added until decolorization. The solution was evaporated in vacuo and the peptide precipitated with diethylether. The crude peptides were dissolved in water (50-100 mg/ml) and purified by reverse-phase high-performance liquid chromatography (RP-HPLC). HPLC conditions were: column: Vydac TP21810C18 (10×250 mm); elution system: gradient system of 0.1% TFA in water v/v (A) and 0.1% TFA in acetonitrile (ACN) v/v (B); flow rate 6 ml/min; absorbance was detected from 190-370 nm. There were different gradient systems used. For example for peptides LQG and LQGV (SEQ ID NO:1): 10 minutes 100% A followed by linear gradient 0-10% B in 50 minutes. For example for peptides VLPALP (SEQ ID NO:4) and VLPALPQ (SEQ ID NO:13): 5 minutes 5% B followed by linear gradient 1% B/minute. The collected fractions were concentrated to about 5 ml by rotation film evaporation under reduced pressure at 40° C. The remaining TFA was exchanged against acetate by eluting two times over a column with anion exchange resin (Merck II) in acetate form. The elute was concentrated and lyophilised in 28 hours. Peptides later were prepared for use by dissolving them in PBS.

RAW 264.7 macrophages, obtained from American Type Culture Collection (Manassas, Va.), were cultured at 37° C. in 5% CO2 using DMEM containing 10% FBS and antibiotics (100 U/ml of penicillin, and 100 µg/ml streptomycin). Cells (1×10$^6$/ml) were incubated with peptide (10 µg/ml) in a volume of 2 ml. After 8 h of cultures cells were washed and prepared for nuclear extracts.

Nuclear extracts and EMSA were prepared according to Schreiber et al. Methods (Schreiber et al. 1989, Nucleic Acids Research 17). Briefly, nuclear extracts from peptide stimulated or nonstimulated macrophages were prepared by cell lysis followed by nuclear lysis. Cells were then suspended in 400 µl of buffer (10 mM HEPES (pH 7.9), 10 mM KCl, 0.1 mM KCL, 0.1 mM EDTA, 0.1 mM EGTA, 1 mM DTT, 0.5 mM PMSF and protease inhibitors), vigorously vortexed for 15 s, left standing at 4° C. for 15 min, and centrifuged at 15,000 rpm for 2 min. The pelleted nuclei were resuspended in buffer (20 mM HEPES (pH 7.9), 10% glycerol, 400 mM NaCl, 1 mM EDTA, 1 mM EGTA, 1 mM DTT, 0.5 mM PMSF and protease inhibitors) for 30 min on ice, then the lysates were centrifuged at 15,000 rpm for 2 min. The supernatants containing the solubilized nuclear proteins were stored at −70° C. until used for the Electrophoretic Mobility Shift Assays (EMSA).

Electrophoretic mobility shift assays were performed by incubating nuclear extracts prepared from control (RAW 264.7) and peptide treated RAW 264.7 cells with a 32P-labeled double-stranded probe (5' AGCTCAGAGGGG-GACTTTCCGAGAG 3' (SEQ ID NO:28)) synthesized to represent the NF-kappaB binding sequence. Shortly, the probe was end-labeled with T4 polynucleotide kinase according to manufacturer's instructions (Promega, Madison, Wis.). The annealed probe was incubated with nuclear extract as follows: in EMSA, binding reaction mixtures (20 µl) contained 0.25 µg of poly(dI-dC) (Amersham Pharmacia Biotech) and 20,000 rpm of 32P-labeled DNA probe in binding buffer consisting of 5 mM EDTA, 20% Ficoll, 5 mM DTT, 300 mM KCl and 50 mM HEPES. The binding reaction was started by the addition of cell extracts (10 µg) and was continued for 30 min at room temperature. The DNA-protein complex was resolved from free oligonucleotide by electrophoresis in a 6% polyacrylamide gel. The gels were dried and exposed to x-ray films.

The transcription factor NF-kB participates in the transcriptional regulation of a variety of genes. Nuclear protein extracts were prepared from LPS and peptide treated RAW264.7 cells or from LPS treated RAW264.7 cells. In order to determine whether the peptide modulates the translocation of NF-kB into the nucleus, on these extracts EMSA was performed. Here we see that indeed some peptides are able to modulate the translocation of NF-kB since the amount of labeled oligonucleotide for NF-kB is reduced. In this experiment peptides that show the modulation of translocation of NF-kB are: VLPALPQVVC (SEQ ID NO:21), LQGV-LPALPQ (SEQ ID NO:21), LQG, LQGV (SEQ ID NO:1), GVLPALPQ (SEQ ID NO:23), VLPALP (SEQ ID NO:4), VLPALPQ (SEQ ID NO:13), GVLPALP (SEQ ID NO:16), VVC, MTRV (SEQ ID NO:20), MTR.

RAW 264.7 mouse macrophages were cultured in DMEM, containing 10% or 2% FBS, penicillin, streptomycin and glutamine, at 37° C., 5% CO$_2$. Cells were seeded in a 12-wells plate (3×10$^6$ cells/ml) in a total volume of 1 ml for 2 hours and then stimulated with LPS (*E. coli* 026:B6; Difco Laboratories, Detroit, Mich., USA) and/or NMPF (1 microgr/ml).

After 30 minutes of incubation plates were centrifuged and cells were collected for nuclear extracts. Nuclear extracts and EMSA were prepared according to Schreiber et al. Cells were collected in a tube and centrifuged for 5 minutes at 2000 rpm (rounds per minute) at 4° C. (Universal 30 RF, Hettich Zentrifuges). The pellet was washed with ice-cold Tris buffered saline (TBS pH 7.4) and resuspended in 400 µl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche) and left on ice for 15 minutes. Twenty-five microliters 10% NP-40 was added and the sample was centrifuged (2 minutes, 4000 rpm, 4° C.). The supernatant (cytoplasmic fraction) was collected and stored at −70° C. The pellet, which contains the nuclei, was washed with 50 µl buffer A and resuspended in 50 µl buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples were left to shake at 4° C. for at least 60 minutes. Finally, the samples were centrifuged and the supernatant (nucleic fraction) was stored at −70° C.

Bradford reagent (Sigma) was used to determine the final protein concentration in the extracts. For Electrophoretic mobility shift assays an oligonucleotide representing NF-κB binding sequence (5' AGCTCAGAGGGGGACTTTC-CGAGAG 3' (SEQ ID NO:28)) was synthesized. Hundred pico mol sense and antisense oligo were annealed and labeled with γ-$^{32}$P-dATP using T4 polynucleotide kinase according to manufacture's instructions (Promega, Madison, Wis.). Nuclear extract (5-7.5 µg) was incubated for 30 minutes with 75000 cpm probe in binding reaction mixture (20 microliter) containing 0.5 µg poly dI-dC (Amersham Pharmacia Biotech) and binding buffer BSB (25 mM MgCl$_2$, 5 mM CaCl$_2$, 5 mM DTT and 20% Ficoll) at room temperature. The DNA-protein complex was resolved from free oligonucleotide by electrophoresis in a 4-6% polyacrylamide gel (150 V, 2-4 hours). The gel was then dried and exposed to x-ray film. The transcription factor NF-kB participates in the transcriptional regulation of a variety of genes. Nuclear protein extracts were prepared from either LPS (1 mg/ml), peptide (1 mg/ml) or LPS in combination with peptide treated and untreated RAW264.7 cells. In order to determine whether the peptides modulate the translocation of NF-kB into the nucleus, on these extracts EMSA was performed. Peptides are able to modulate the basal as well as LPS induced levels of NF-kB. In this experiment peptides that show the inhibition of LPS induced translocation of NF-kB are: VLPALPQVVC (SEQ ID NO:21), LQGVLPALPQ (SEQ ID NO:21), LQG, LQGV (SEQ ID NO:1), GVLPALPQ (SEQ ID NO:23), VLPALP (SEQ ID NO:4), VVC, MTR and circular LQGVL-PALPQVVC (SEQ ID NO:17). Peptides that in this experiment promote LPS induced translocation of NF-kB are: VLPALPQ (SEQ ID NO:13), GVLPALP (SEQ ID NO:16), and MTRV (SEQ ID NO:20). Basal levels of NF-kB in the nucleus was decreased by VLPALPQVVC (SEQ ID NO:21), LQGVLPALPQ (SEQ ID NO:21), LQG and LQGV (SEQ ID NO:1) while basal levels of NF-kB in the nucleus was increased by GVLPALPQ (SEQ ID NO:23), VLPALPQ (SEQ ID NO:13), GVLPALP (SEQ ID NO:16), VVC, MTRV (SEQ ID NO:20), MTR and LQGVLPALPQVVC (SEQ ID NO:17). In other experiments, QVVC (SEQ ID NO:29) also showed the modulation of translocation of NF-kB into nucleus (data not shown).

Further modes of identification of gene-regulatory peptides by NFkB analysis

Cells: Cells will be cultured in appropriate culture medium at 37° C., 5% CO$_2$. Cells will be seeded in a 12-wells plate (usually 1×10$^6$ cells/ml) in a total volume of 1 ml for 2 hours and then stimulated with regulatory peptide in the presence or absence of additional stimuli such as LPS. After 30 minutes of incubation plates will be centrifuged and cells are collected for cytosolic or nuclear extracts.

Nuclear Extracts: Nuclear extracts and EMSA could be prepared according to Schreiber et al. Method (Schriber et al. 1989, Nucleic Acids Research 17). Cells are collected in a tube and centrifuged for 5 minutes at 2000 rpm (rounds per minute) at 4° C. (Universal 30 RF, Hettich Zentrifuges). The pellet is washed with ice-cold Tris buffered saline (TBS pH 7.4) and resuspended in 400 µl of a hypotonic buffer A (10 mM HEPES pH 7.9, 10 mM KCl, 0.1 mM EDTA, 0.1 mM EGTA, 1 mM DTT, 0.5 mM PMSF and protease inhibitor cocktail (Complete™ Mini, Roche) and left on ice for 15 minutes. Twenty five micro liter 10% NP-40 is added and the sample is centrifuged (2 minutes, 4000 rpm, 4° C.). The supernatant (cytoplasmic fraction) was collected and stored at −70° C. for analysis. The pellet, which contains the nuclei, is washed with 50 µl buffer A and resuspended in 50 µl buffer C (20 mM HEPES pH 7.9, 400 mM NaCl, 1 mM EDTA, 1 mM EGTA, 1 mM DTT, 0.5 mM PMSF and protease inhibitor cocktail and 10% glycerol). The samples are left to shake at 4° C. for at least 60 minutes. Finally the samples are centrifuged and the supernatant (nucleic fraction) is stored at −70° C. for analysis.

Bradford reagent (Sigma) could be used to determine the final protein concentration in the extracts.

EMSA: For Electrophoretic mobility shift assays an oligonucleotide representing NF-κB binding sequence such as (5' AGCTCAGAGGGGGACTTTCCGAGAG 3' (SEQ ID NO:28)) are synthesized. Hundred pico mol sense and antisense oligo are annealed and labeled with γ-$^{32}$P-dATP using T4 polynucleotide kinase according to manufacture's instructions (Promega, Madison, Wis.). Cytosolic extract or nuclear extract (5-7.5 µg) from cells treated with regulatory peptide or from untreated cells is incubated for 30 minutes with 75000 cpm probe in binding reaction mixture (20 µL) containing 0.5 µg poly dI-dC (Amersham Pharmacia Biotech) and binding buffer BSB (25 mM MgCl$_2$, 5 mM CaCl$_2$, 5 mM DTT and 20% Ficoll) at room temperature. Or cytosolic and nuclear extract from untreated cells or from cells treated with stimuli could also be incubated with probe in binding reaction mixture and binding buffer. The DNA-protein complex is resolved from free oligonucleotide by electrophoresis in a 4-6% polyacrylamide gel (150 V, 2-4 hours). The gel is then dried and exposed to x-ray film. Peptides can be biotinylated and incubated with cells. Cells are then washed with phosphate-buffered saline, harvested in the absence or presence of certain stimulus (LPS, PHA, TPA, anti-CD3, VEGF, TSST-1, VIP or know drugs etc.). After culturing cells are lysed and cells lysates (whole lysate, cytosolic fraction or nuclear fraction) containing 200 micro gram of protein are incubated with 50 microliter Neutr-Avidin-plus beads for 1 h at 4° C. with constant shaking. Beads are washed five times with lysis buffer by centrifugation at 6000 rpm for 1 min. Proteins are eluted by incubating the beads in 0.05 N NaOH for 1 min at room temperature to hydrolyze the protein-peptide linkage and analyzed by SDS-polyacrylamide gel electrophoresis followed by immunoprecipitated with agarose-conjugated anti-NF-kB subunits antibody or immunoprecipitated with antibody against to be studied target. After hydrolyzing the protein-peptide linkage, the sample could be analyzed on HPLS and mass-spectrometry. Purified NF-kB subunits or cell lysate interaction with biotinylated regulatory peptide can be analyzed on biosensor technology. Peptides can be labeled with FITC and incubated with cells in the absence or presence of different stimulus. After culturing, cells can be analyzed with fluorescent microscopy, confocal microscopy, flow cytometry (cell membrane staining and/or intracellular staining) or cells lysates are made and analyzed on HPLC and mass-spectrometry. NF-kB transfected (reporter gene assay) cells and gene array technology can be used to determine the regulatory effects of peptides.

HPLC and mass-spectrometry analysis: Purified NF-kB subunit or cytosolic/nuclear extract is incubated in the absence or presence of (regulatory) peptide is diluted (2:1) with 8 N guanidinium chloride and 0.1% trifluoroacetic acid, injected into a reverse-phase HPLC column (Vydac C18) equilibrated with solvent A (0.1% trifluoroacetic acid), and eluted with a gradient of 0 to 100% eluant B (90% acetonitrile in solvent A). Factions containing NF-kB subunit are pooled and concentrated. Fractions are then dissolved in appropriate volume and could be analyzed on mass-spectrometry.

See also PCT International Publications WO99/59671, WO01/72831, WO97/49721, WO01/10907, WO01/11048, the contents of each of which are herein incorporated by this reference.

FURTHER EXAMPLES

In this study we demonstrate that LQGV (SEQ ID NO:1), AQGV (SEQ ID NO:2), and LAGV (SEQ ID NO:10), administrated after the induction of hemorrhagic shock in rats, significantly reduced TNF-α and IL-6 plasma levels, which is associated with reduced TNF-α and IL-6 mRNA transcript levels in the liver. This indicates that LQGV (SEQ ID NO:1), AQGV (SEQ ID NO:2), LAGV (SEQ ID NO:10) may have therapeutic potential with beneficial effects on systemic inflammation, thereby reducing organ integrity/function, which is associated with shock and SIRS often seen with severe burns patients.

Materials and Methods

Adult Male specific pathogen-free Wistar rats (Harlan CPB, Zeist, NL), weighing 350-400 g were used after a minimum seven-day acclimation period. The animals were housed under barrier conditions and kept at 25° C. with a twelve-hour light/dark cycle. Rats were allowed free access to water and chow (−). All procedures were performed in accordance with the *Principles of Laboratory Animal Care* (NIH publication No. 86-23, revised 1985) under a protocol approved by the Committee on Animal Research of the Erasmus University (protocol EUR 365).

The rats were fasted overnight but were allowed free access to water before the experiment. Subsequent to endotracheal intubation the rats were mechanically ventilated with an isofluorane (−) $N_2O/O_2$ mixture at 60 breaths/minute. Body temperature was continuously maintained at 37.5° C. by placing the animals on a thermo controlled "half-pipe" (UNO, NL). Polyethylene tubes (PE-50, Becton Dickinson; St. Michielsgestel, NL) were flushed with heparin and placed via the right carotid artery in the aorta and in the right internal jugular vein. The animals received no heparin before or during the experiment.

Mean arterial pressures (MAP) was measured using transducers (Becton Dickinson) that were connected in line to an electronic recorder (Hewlett Packard, 78354-A Germany) for electronically calculated mean pressures and continuous measurement of the animal's blood pressure. Under semi sterile conditions a median laparotomy was performed and ultrasonic perivascular flow probes (Transonic Systems Inc, Maastricht, NL) were placed on the common hepatic artery and the portal vein. A supra pubic catheter was placed to monitor the urine production during and after resuscitation.

After an acclimatization period of 20 minutes, the rats were randomized into the following five groups:

Hemorrhagic shock group were bled within ten minutes to a mean arterial pressure (MAP) of 40 mmHg and maintained at this level for 60 minutes by withdrawing or re-infusing shed blood as needed. Thereafter, the animals were resuscitated with plus minus four times the volume of the withdrawn blood over 30 minutes with a 0.9% NaCl solution.

The hemorrhagic shock group+peptide A (LAGV (SEQ ID NO:10); one-letter amino acid code) underwent the same procedure as the hemorrhagic shock group but received a single bolus injection of 5 mg/kg peptide A intravenously 30 minutes after the induction of shock.

The hemorrhagic shock group+peptide B (AQGV (SEQ ID NO:2)) underwent the same procedure as the hemorrhagic shock group and received a single bolus injection of 5 mg/kg peptide B intravenously, 30 minutes after the induction of shock.

The hemorrhagic shock group+peptide C (LQGV (SEQ ID NO:1)) underwent the same procedure as the hemorrhagic shock group and received a single bolus injection of 5 mg/kg peptide C intravenously, 30 minutes after the induction of shock.

Sham group underwent the same procedure as the hemorrhagic shock group without performing the hemorrhage or administration of any kind of peptides.

The hepatic arterial blood flow (QHA) and hepatic portal venous blood flow (QVP) were measured with transit time ultrasonic perivascular flow probes, connected to an ultrasonic meter (T201; Transonic Systems, Inc., Maastricht, NL). Systemic and hepatic hemodynamics were continuously measured. At regular time points arterial blood samples were taken. The animals were euthanized by withdrawal of arterial blood via the carotid artery.

Blood, Tissue, and Cell Harvesting Procedure

Plasma collection and storage: Whole arterial blood was obtained at −15, 30, 60, 90, 120, 150 and 180 minutes after induction of shock via the right carotid artery and collected in duplo. 0.2 ml was placed in tubes (Eppendorf EDTA KE/1.3) to be assayed in the coulter counter (−). 0.5 ml was placed in MINICOLLECT™ tubes (Bio-one, Greiner) centrifuged for five minutes, immediately frozen, and stored at −80° C., until assayed. All assays were corrected for the hematocrit.

Measurement of cytokines (still in progress): The levels of IL-6, and IL-10 in the serum were determined by an ELISA (R&D Systems Europe Ltd.) according to the manufacturer's instructions.

Histology (still in progress): The alterations in lung, liver, sigmoid and small bowel morphology were examined in sham-operated animals, in animals after trauma-hemorrhage and in animals after trauma-hemorrhage treated with peptide A, B or C. All tissues were collected in duplo. One part was harvested and fixed in formalin (Sigma) and later embedded in paraffin. The other part was placed in tubes (NUNC Cryo Tube™ Vials), quick frozen in liquid nitrogen and stored at −80° C. until assayed.

Results

Mean Arterial Pressure: MAP dropped in all shock groups significant during the shock phase compared to the control group.

Hematocrit: The hematocrit following trauma-hemorrhage was similar in the different peptide A, B and C treated and non-treated groups. During the shock phase there was a difference of hematocrit in the control group in comparison with the other groups. From the resuscitation phase (90 minutes) there was no significant difference in hematocrit among the control, trauma-hemorrhage, and peptide groups.

Leukocyte Recruitment: During trauma-hemorrhage the leukocytes dropped from 100% at T0 in all groups to a minimum of 40.0±11.9%, 42.0±8.7%, 47.3±12.4%, 38.2±7.4% in respectively the non-treated, peptide A treated, peptide B treated and peptide C treated group because of leukocyte accumulation in the splanchnic microcirculation. There was a significant difference in leukocyte concentration between all treated and non-treated trauma-hemorrhage groups, and the control group during the shock phase. No significant difference was noticed between the peptide A, B or C treated animals and the non-treated animals.

Blood Concentrations Of Macrophages And Granulocytes: At 180 min after the onset of trauma-hemorrhage, concentrations of circulating macrophages ($M_\Phi$) and granulocytes were significant lower in the peptide B and C treated animals compared with the corresponding experimental group. Blood levels of circulating $M_\Phi$ and granulocytes were 5,556±1,698 $10^9/l$ in sham-operated animals whereas blood levels were 6,329±1,965 $10^9/l$ after trauma-hemorrhage, and decreased by 29.9% after administration of peptide B (4,432±0.736 $10^9/l$) and 39.2% after administration of peptide C (3,846±0.636 $10^9/l$) compared with concentrations after trauma-hemorrhage.

Arterial Hepatic Blood Flow: There was a decrease in the arterial hepatic blood flow in the shock group (18.3±14.3%) and in the peptide A (21.3±9.1%), B (18.1±9.0%) and C (21.2±8.6%) group during the shock period compared with the control group (102.6±23.5%). An increase in blood flow was observed during the reperfusion in the hepatic artery of the shock group (128.9±75.4%) compared with control animals (83.7±24.2%) and the animals treated with peptide B (78.4±28.3%).

Trauma-hemorrhage results in hypoxic stress owing to the absolute reduction in circulating blood volume. In contrast, sepsis is an inflammatory state mainly mediated by bacterial products. It is interesting that these divergent insults reveal similar pathophysiologic alterations in terms of the splanchnic circulation.

Hemorrhagic shock significantly increases leukocyte accumulation in the splanchnic microcirculation owing to the up-regulation of P selectin. The expression of intercellular adhesion molecule within the intestinal muscular vasculature after hemorrhagic shock promotes the local recruitment of leukocytes, and this inflammatory response is accompanied by subsequent impairment of intestinal function.

The adhesion and extravasation of neutrophils not only contribute to the inflammatory response in the splanchnic tissue bed but also induce intestinal microcirculatory failure and dysfunction after severe stress. This is mediated by the induced expression of adhesion molecules, such as selectins and endothelial cell adhesion molecules, on the surface of neutrophils and endothelial cells.

In our shock experiments, leukocyte concentration significant decreases during hemorrhagic shock compared to the control animals. However a single dose of peptide B or C administered during resuscitation, decreased concentrations of circulating macrophages and granulocytes 120 minutes after the onset of hemorrhagic shock compared to the non-treated animals.

Because some female sex hormones effectively protect the organs from circulatory failure after various adverse circulatory conditions, numerous studies have been performed to clarify the molecular mechanism of for example estradiol action with regard to tissue circulation. In this study, a single dose of peptide was administered following trauma-hemorrhage and various parameters were measured at 3 hours following the induction of sepsis. Treatment with peptides improved or restored immune functional parameters and cardiovascular functions. Therefore, our results show that administration of short oligopeptides (NMPFs) is beneficial in the treatment of critically ill trauma victims experiencing hemorrhagic shock.

Example 2

BACKGROUND: Hemorrhagic shock followed by resuscitation induces a massive pro-inflammatory response, which may culminate into severe inflammatory response syndrome, multiple organ failure and finally death. Treatments aimed at inhibiting the effects of pro-inflammatory cytokines are only effective when initiated before the onset of hemorrhagic shock, which severely limits their clinical application.

AIM: We investigated whether the administration of synthetic hCG-related oligopeptides (LQGV (SEQ ID NO: 1), AQGV (SEQ ID NO:2), LAGV (SEQ ID NO:10)) 30 minutes after induction of hemorrhagic shock reduced the inflammatory response.

METHODS: Rats were bled to 50% of baseline mean arterial pressure and one hour later resuscitated by autologous blood transfusion. Thirty minutes after onset of hemorrhagic shock, experimental groups received either one of the synthetic hCG-related oligopeptides (LQGV (SEQ ID NO:1), AQGV (SEQ ID NO:2), LAGV (SEQ ID NO:10)) or 0.9% NaCl solution. TNF-α and IL-6 plasma levels were determined at fixed time points before and after onset of hemorrhagic shock. Liver, lungs, ileum and sigmoid mRNA levels for TNF-α, IL-6 and ICAM-1 were determined 180 minutes after onset of hemorrhage.

RESULTS: Treatment with either one of the three hCG-related oligopeptides (LQGV (SEQ ID NO:1), AQGV (SEQ ID NO:2), LAGV (SEQ ID NO:10)) efficiently reduced TNF-α and IL-6 plasma levels as well as TNF-α and IL-6 mRNA transcript levels in the liver.

CONCLUSION: Considering these powerful effects of hCG-related oligopeptides during severe hemorrhagic shock, they may have therapeutic potential with beneficial effects on the hyper inflammation, thereby reducing the late life threatening tissue- and organ-damage that is associated with severe hemorrhagic shock.

INTRODUCTION: In hemorrhagic shock there is massive blood loss, which cannot be compensated by the body without treatment. The primary treatment of hemorrhagic shock is to control bleeding and restore intravascular volume to improve tissue perfusion. This treatment induces an inflammatory response, which may culminate into a severe inflammatory response and finally multiple organ dysfunction syndrome (MODS) [1, 2, 3]. In addition, approximately 40% of patients develop sepsis as a result of trauma-hemorrhage [3]. Sepsis and MODS are the leading causes of death in critically ill patients on the intensive care unit all over the world with mortality rates of about 50% [4, 5].

The severe inflammatory response due to trauma-hemorrhage is characterized by increased expression of adhesion molecules, such as intracellular adhesion molecule-1 (ICAM-1) and vascular cell adhesion molecule-1 (VCAM-1), on sinusoidal endothelial cells and hepatocytes. Furthermore, increased levels of pro-inflammatory cytokines are found systemically and locally in liver, lungs and intestine [6, 7, 8, 9]. The pro-inflammatory cytokines produced are in particular tumor necrosis factor alpha (TNF-α), interleukin (IL)-1β and IL-6 [10, 11, 12]. These cytokines affect organ integrity/function directly, but also indirectly through secondary mediators, such as nitric oxide, thromboxanes, leukotrienes, platelet-activating factor, prostaglandins, and complement [13, 14]. TNF-α also causes the release of tissue-factor by endothelial cells leading to fibrin deposition and disseminated intravascular coagulation [15, 16]. Cells within the liver, mainly Kupffer cells, but also hepatocytes and sinusoidal endothelial cells, are considered as the main producers of these pro-inflammatory cytokines during hemorrhagic shock [17].

The last decade, researchers have focused on the modulation of the systemic inflammatory responses with therapeutic agents aiming at neutralizing the activity of cytokines, especially TNF-α [18]. Other researchers used therapeutic agents aiming at the inhibition of TNF-α production [19]. However, most of these therapeutic agents must be administered before the onset of hemorrhagic shock to achieve a therapeutic effect [19]. Clearly, this is almost impossible in a clinical trauma-hemorrhage setting. Therefore, therapies initiated after the onset of severe trauma-hemorrhage and aiming at reducing the production of pro-inflammatory cytokine are more relevant to prevent the events leading to MODS.

During pregnancy, the maternal immune system tolerates the fetus by reducing the cell-mediated immune response while retaining normal humoral immunity [20]. Also, clinical symptoms of cell-mediated autoimmune diseases regress in many patients during pregnancy [20]. The hormone human chorionic gonadotropin (hCG) is mainly secreted by placental syncytiocytotrophoblasts during pregnancy and has been shown to be immunoregulatory.[21, 22, 23]. The β-subunit of hCG is degraded by specific proteolytic enzymes [24]. This can lead to the release of several oligopeptides consisting of four to seven amino acids which, because of their role in regulation of physiological processes, are considered regulatory [25]. We successfully demonstrated that synthetic hCG-related oligopeptides can inhibit the acute inflammatory response, disease severity, and mortality in high-dose lipopolysaccharide induced systemic inflammatory response syndrome [26]. Considering these powerful regulating effects of synthetic hCG-related oligopeptides on inflammation, we hypothesized that the administration of such regulatory oligopeptides after severe trauma-hemorrhage could inhibit the massive inflammatory response, associated with this condition. To this end, we used LQGV (SEQ ID NO:1), which is part of the primary structure of loop two of the β-subunit of hCG, and two alanine replacement variants, namely AQGV (SEQ ID NO:2) and LAGV (SEQ ID NO:10).

In this study we demonstrate that LQGV (SEQ ID NO:1), AQGV (SEQ ID NO:2) and LAGV (SEQ ID NO:10), administrated after the induction of hemorrhagic shock in rats, significantly reduced TNF-α and IL-6 plasma levels, which is associated with reduced TNF-α and IL-6 mRNA transcript levels in the liver. This indicates that LQGV (SEQ ID NO:1), AQGV (SEQ ID NO:2), LAGV (SEQ ID NO:10) may have therapeutic potential with beneficial effects on systemic inflammation, thereby reducing organ integrity/function, which is associated with severe hemorrhagic shock.

Materials and Methods

Animals

Adult male specific pathogen-free Wistar rats (Harlan CPB, Zeist, NL), weighing 350-400 g were used. Animals were housed under barrier conditions at 25° C. with a twelve-hour light/dark cycle, and were allowed food and water ad libitum. The experimental protocol was approved by the Animal Experiment Committee under the Dutch Experiments on Animals Act and adhered to the rules laid down in this national law that serves the implementation of "Guidelines on the protection of experimental animals" by the Council of Europe (1986), Directive 86/609/EC.

hCG-related synthetic oligopeptides: The hCG-related oligopeptides (LQGV (SEQ ID NO:1), AQGV (SEQ ID NO:2) and LAGV (SEQ ID NO:10)) were synthesized by Ansynth Service B.V. (Roosendaal, NL) and dissolved in 0.9% NaCl at a concentration of 10 mg/ml.

Surgical procedures: Rats were food deprived overnight before the experiment, but were allowed water ad libitum. Rats were anesthetized using a mixture of $N_2O/O_2$ isoflurane (Pharmachemie B. V, Haarlem, NL). Body temperature was continuously maintained at 37.5° C. by placing the rats on a thermo controlled 'half-pipe' (UNO, Rotterdam, NL). Endotracheal intubation was performed, and rats were ventilated at 60 breaths per minute with a mixture of $N_2O/O_2$ 2% isoflurane. Polyethylene tubes (PE-50, Becton Dickinson; St. Michielsgestel, NL) were flushed with heparin and placed via the right carotid artery in the aorta and in the right internal jugular vein. The rats received no heparin before or during the experiment.

Figure 7:
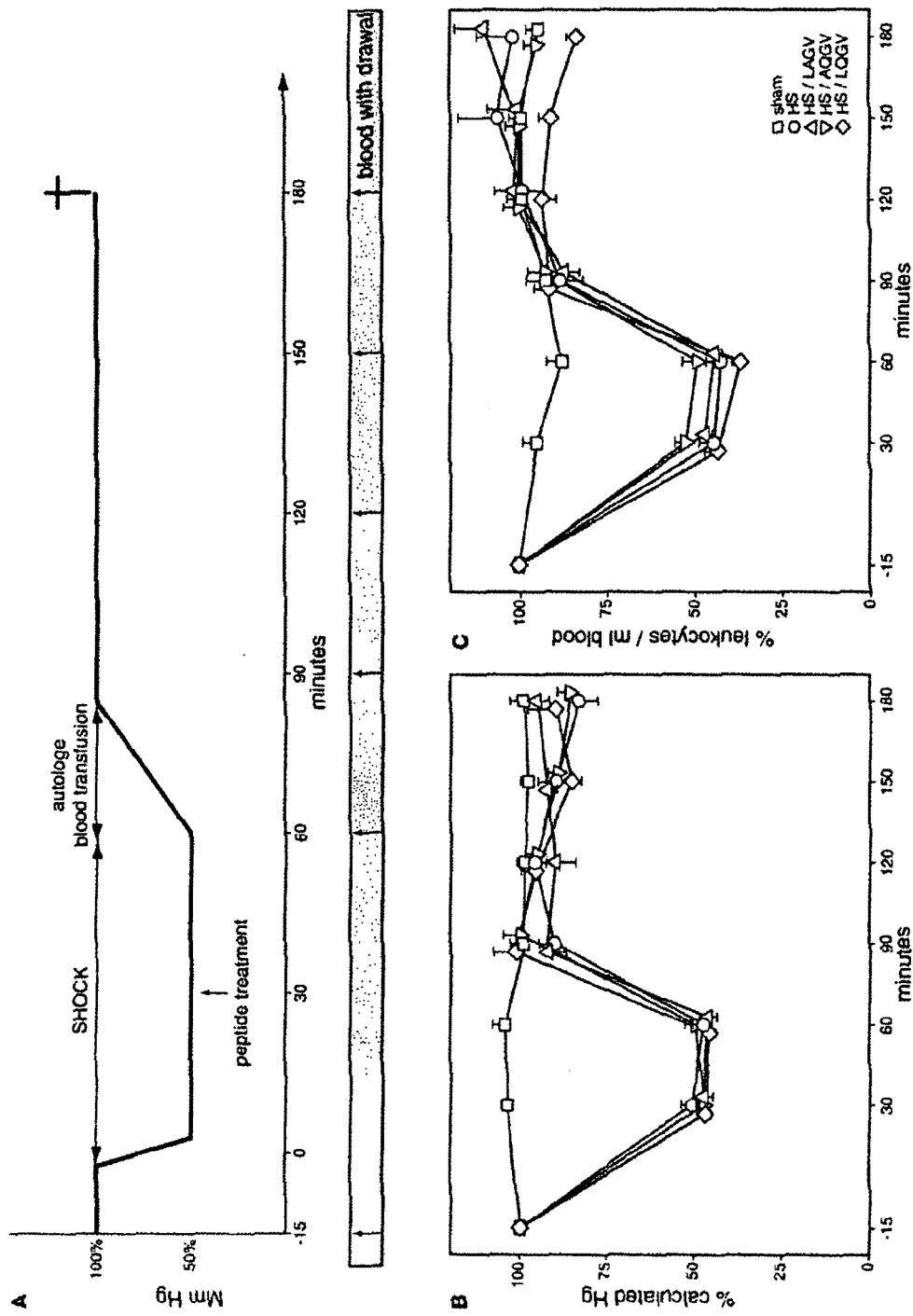
FIG. 7. Hemorrhagic shock model. A) Schematic representation of the experimental design. B) The measured mmHg was recalculated in percentages to standardize the experiment and to compensate for animal differences. C) Percentage of leukocytes in blood during various time points of the experiment.

Experimental procedures: After an acclimatization period of 15 minutes, the rats were randomized into five different groups: 1) sham, 2) hemorrhagic shock (HS), 3) hemorrhagic shock with LQGV (SEQ ID NO:1) treatment (HS/LQGV (SEQ ID NO:1)), 4) hemorrhagic shock with AQGV (SEQ ID NO:2) treatment (HS/AQGV (SEQ ID NO:2)) and 5) hemorrhagic shock with LAGV (SEQ ID NO:10) treatment (HS/LAGV (SEQ ID NO:10)). Hemorrhagic shock was induced by blood withdrawal, reducing the circulating blood volume until a mean arterial pressure (MAP) of 50% of normal mmHg was reached. This level of hypotension was maintained for 60 minutes. After 30 minutes, rats received either a single bolus injection of 10 mg/kg LQGV (SEQ ID NO:1), AQGV (SEQ ID NO:2), LAGV (SEQ ID NO:10) or 0.9% NaCl solution. The peptides and dosage were based on previous studies, in which we performed dose-escalation experiments (manuscript in preparation). Sixty minutes after induction of hemorrhagic shock, rats were resuscitated by autologous blood transfusion over a period of 30 minutes and monitored for another 120 minutes after which they were sacrificed (FIG. 7A). Sham animals underwent the same surgical procedure as the hemorrhagic shock animals, but without performing hemorrhage and administration of peptides.

Plasma collection and storage: Arterial blood was obtained 15 minutes before and 30, 60, 90, 120, 150 and 180 minutes after onset of hemorrhage (FIG. 7A). After blood withdrawal, leukocyte numbers were determined using a coulter counter (Beckman Coulter, Mijdrecht, NL) and corrected for the hematocrit. Approximately, 0.3 ml of blood was placed into mini collect tubes (Greiner, Bio-one, Alphen a/d Rijn, NL), plasma was obtained by centrifugation (1500 r.p.m.; 5 minutes), immediately frozen, and stored at −80° C., until assayed.

Measurements of Mean arterial pressure: During the experiments, mean arterial pressure (MAP) was continuously measured using transducers (Becton Dickinson) that were connected in line to an electronic recorder (Hewlett Packard, 78354-A, Germany).

Tissue collection and storage: Liver, lungs, ileum and sigmoid were surgically removed at the end of the experiment, snap-frozen, and stored at −80° C., until assayed.

Measurement of cytokines: TNF-α and IL-6 plasma levels were determined by ELISA (R&D Systems Europe Ltd, Abingdon, UK), according to the manufacturer's instructions.

Evaluation of mRNA levels by real-time quantitative (RQ)-PCR: RNA was isolated using a QIAGEN kit (QIAGEN, Hilden, Germany), according to the manufacturer's instructions. TNF-α, IL-6 and ICAM-1 transcripts were determined by RQ-PCR using an Applied Biosystems 7700 PCR machine (Foster City, Calif., USA) as described previously [27]. TNF-α, IL-6 and ICAM-1 expression was quantified by normalization against GAPDH. Primer probe combinations used are listed in Table 1.

Statistical analysis: Statistical analysis was performed using SPSS version 11 software (SPSS Inc., Chicago, Ill.). Inter group differences were analyzed with Kruskal-Wallis statistical test. If Kruskal-Wallis statistical testing resulted in a p<0.05, a Dunn's Multiple Comparison test was performed and p<0.05 was considered statistically significant.

Results

Induction of hemorrhagic shock. Lowering the MAP to 50% of normal induced hemorrhagic shock, which was successfully maintained for 60 minutes in all four experimental groups (FIG. 7B). No change in MAP was observed in sham treated rats (FIG. 7B). A decrease in the percentage of blood leukocytes was observed in all four experimental groups after blood withdrawal (FIG. 7C). Sixty minutes after hemorrhagic shock, rats were resuscitated with there own blood to induce organ reperfusion, which was associated with a normalization of leukocyte level (FIG. 7C).

Figure 8:
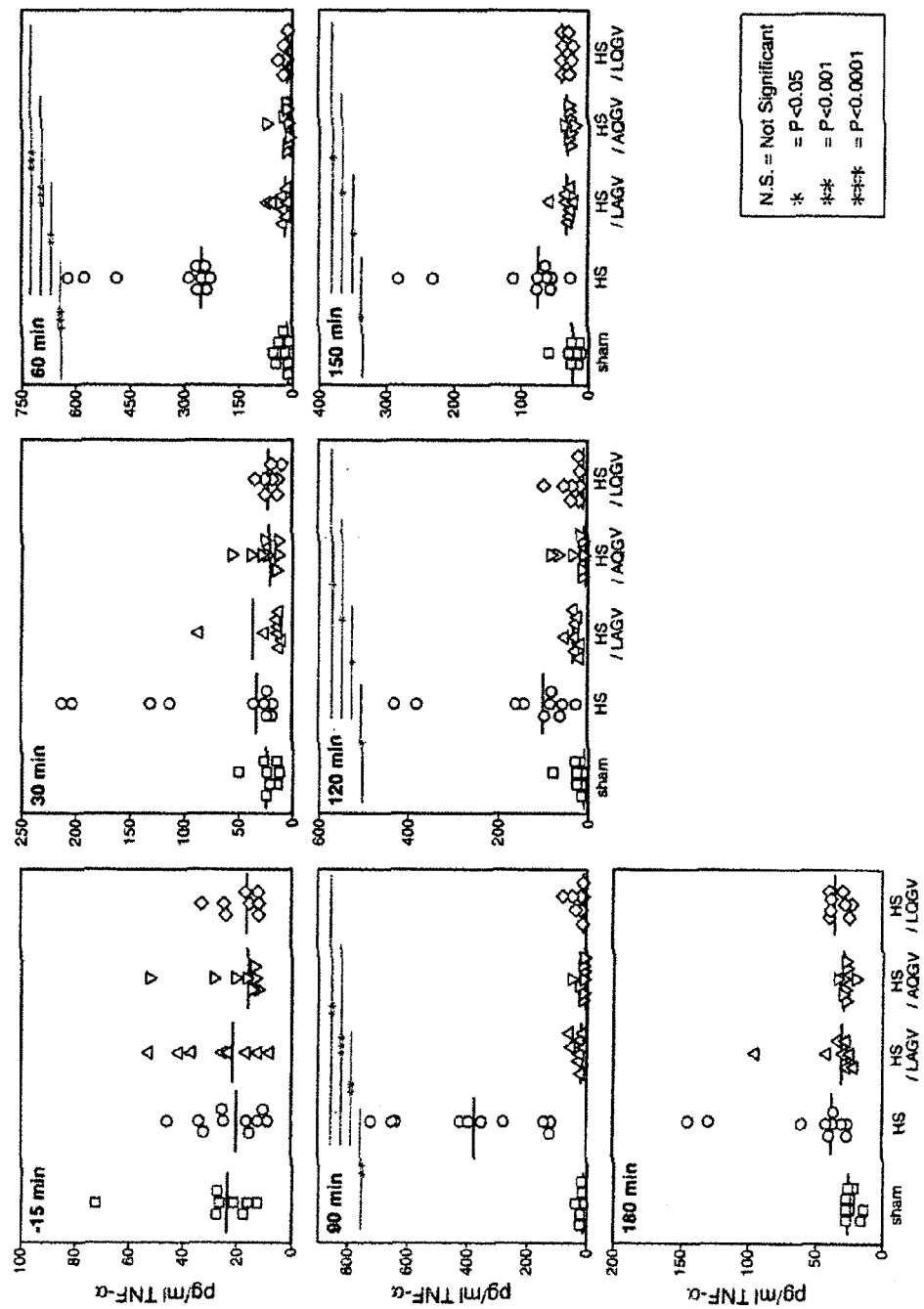
FIG. 8. TNF-α plasma levels in different experimental groups determined at 15 minutes before and 30, 60, 90, 120, 150 and 180 minutes after the onset of hemorrhagic shock. (Sham, O HS, ∇ HS/LQGV (SEQ ID NO:1), ◇ HS/AQGV (SEQ ID NO:2), Δ HS/LAGV (SEQ ID NO:10). Each figure represents one animal.
Figure 9:
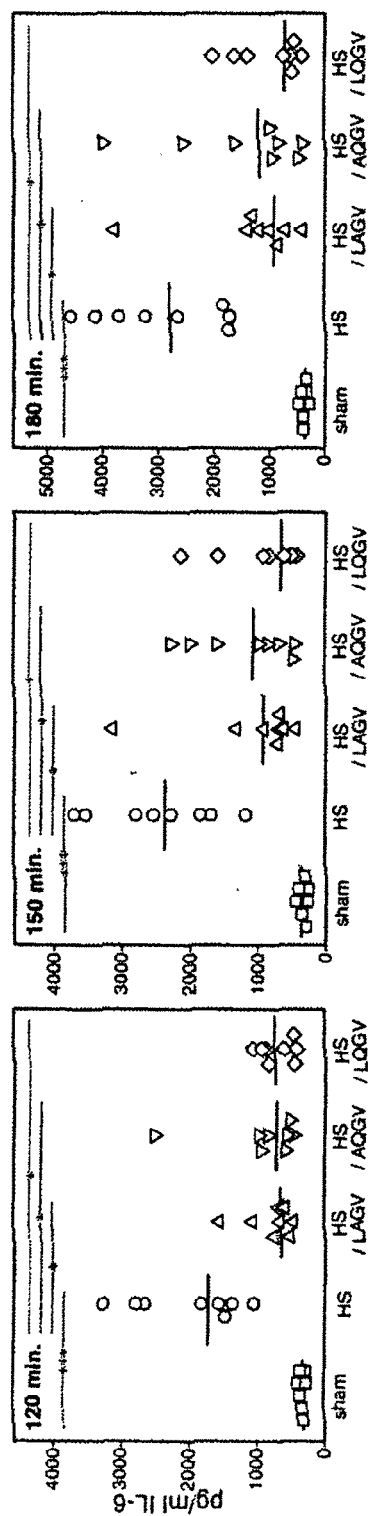
FIG. 9. IL-6 plasma levels in different experimental groups determined at 120, 150 and 180 minutes after the onset of hemorrhagic shock □ Sham, O HS, ∇ HS/LQGV (SEQ ID NO:1), ◇ HS/AQGV (SEQ ID NO:2), Δ HS/LAGV (SEQ ID NO:10). Each figure represents one animal.

Oligopeptide treatment reduces pro-inflammatory cytokine plasma levels: The therapeutic capacity of three synthetic oligopeptides (LQGV (SEQ ID NO:1), AQGV (SEQ ID NO:2), LAGV (SEQ ID NO:10)) related to the primary structure of loop two of the β-subunit of hCG was evaluated in a rat hemorrhagic shock model. Before induction of hemorrhage, TNF-α plasma levels were comparable in all five groups (~15-24 pg/ml) (FIG. 8). In the HS group, TNF-α levels started to increase thirty minutes after induction of hemorrhagic shock and were significantly increased after sixty minutes, as compared to the sham group (264 pg/ml vs. 24 pg/ml, respectively; p<0.01). TNF-α levels reached a maximum of 374 pg/ml after 90 minutes in the HS group, after which levels declined again but always remaining increased compared to the sham group (FIG. 8). In contrast, none of the oligopeptide-treated HS groups (HS/LQGV (SEQ ID NO:1), HS/AQGV (SEQ ID NO:2), HS/LAGV (SEQ ID NO:10)) showed an increase in plasma TNF-α levels during the experiment (FIG. 8). IL-6 levels are known to increase at a later time-point than TNF-α after severe hemorrhagic shock [11, 12]. Therefore, we determined IL-6 levels in blood samples collected 120, 150 and 180 minutes after the onset of hemorrhagic shock. In the HS group, IL-6 plasma levels were significantly increased as compared to sham group at 120 minutes (1704 pg/ml vs. 338 pg/ml, respectively; p<0.001), at 150 minutes (2406 pg/ml vs. 316 pg/ml, respectively; p<0.001) and at 180 minutes (2932 pg/ml vs. 369 pg/ml, respectively; p<0.001) (FIG. 9). Although IL-6 levels tended to increase a little in the HS/oligopeptide treated rats as compared to sham treated rats, this never reached significance. Treatment with oligopeptides after hemorrhagic shock (HS/LQGV (SEQ ID NO:1), HS/AQGV (SEQ ID NO:2), HS/LAGV (SEQ ID NO:10)) resulted in a significant reduction of IL-6 plasma levels as compared to the non-treated hemorrhagic shock group (HS) (FIG. 9). These data demonstrate that treatment with a single dose of either LQGV (SEQ ID NO:1), AQGV (SEQ ID NO:2), or LAGV (SEQ ID NO:10) after induction of hemorrhagic shock results in a significant reduction of TNF-α and IL-6 plasma levels.

Figure 10:
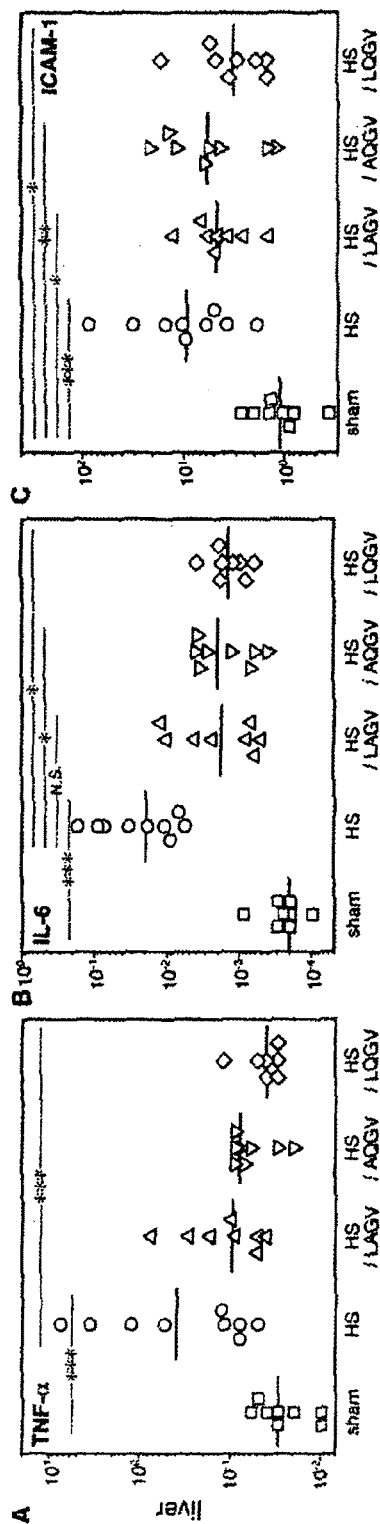
FIG. 10. Transcript levels for A) TNF-α, B) IL-6 and C) ICAM-1 in the liver, 180 minutes after the onset of hemorrhagic shock. Data expressed are correlated to GAPDH expression. □ Sham, O HS, ∇ HS/LQGV (SEQ ID NO:1), ◇ HS/AQGV (SEQ ID NO:2), Δ HS/LAGV (SEQ ID NO:10). Each figure represents one animal.

Oligopeptide treatment reduces TNF-α and IL-6 but not ICAM-1 mRNA levels in the liver: Because oligopeptide treatment clearly decreased the TNF-α and IL-6 plasma levels, we analyzed mRNA levels in liver, lungs, ileum and sigmoid tissues at 180 minutes after the onset of hemorrhagic shock. In the liver, TNF-α transcripts were significantly increased in the HS group as compared to the sham group. Oligopeptide treatment was associated with decreased TNF-α transcripts in the liver as compared to non-treated HS rats with only HS/LQGV (SEQ ID NO:1) showing a significant reduction as compared to HS (p<0.01; FIG. 10A).

In the HS group, IL-6 transcripts in the liver were increased 83 times as compared to the sham group (p<0.001; FIG. 10B). None of the oligopeptide treated groups showed an increase in IL-6 mRNA as compared to the sham treated group. LQGV (SEQ ID NO:1) and AQGV (SEQ ID NO:2) treatment resulted in a significant reduction in IL-6 mRNA transcripts as compared to the HS group (p<0.05; FIG. 10B).

ICAM-1 transcript levels in the liver were significantly increased in the HS group as compared to the sham group (FIG. 10C). Oligopeptide treatment during hemorrhagic shock (HS/LQGV (SEQ ID NO:1), HS/AQGV (SEQ ID NO:2), HS/LAGV (SEQ ID NO:10)) did not affect the ICAM-1 transcript levels in the liver (FIG. 10C). In lungs, ileum and sigmoid tissue no significant differences could be detected between the various groups for TNF-α, IL-6 and ICAM-1 (data not shown). These data indicate that oligopeptide treatment following hemorrhagic shock decreases pro-inflammatory cytokine transcript levels in the liver but does not reduce ICAM-1 transcript levels.

Discussion

In this study we used a rat model of hemorrhagic shock and demonstrated that administration of synthetic hCG-related oligopeptides (LQGV (SEQ ID NO:1), AQGV (SEQ ID NO:2), LAGV (SEQ ID NO:10)) 30 minutes after shock induction, efficiently reduces the pro-inflammatory cytokine levels associated with this condition. Our data demonstrate this to be the consequence of reduced expression of pro-inflammatory cytokine mRNA transcript levels in the liver.

Hemorrhagic shock is associated with an early adherence of leukocytes to the vascular endothelium as a result of a decreased blood volume [28]. In our model, a decrease in the percentage of leukocytes was detected in all four experimental groups after blood withdrawal. This indicates that all experimental groups experienced hemorrhagic induced shock. Resuscitation resulted in an increase of the percentages of leukocytes in the experimental groups.

Hemorrhagic shock followed by resuscitation induces a severe inflammatory response, which is characterized by an exaggerated production of early pro-inflammatory cytokines, such as TNF-α, IL1β, and subsequently IL-6 [10, 11, 12]. TNF-α is a key mediator of the innate immune system that is crucial for the generation of a local protective immune response against infectious or non-infectious agents [9]. However, uncontrolled massive TNF-α production is lethal, as it spreads via the bloodstream into other organs thereby inducing tissue damage and promoting the production of secondary pro-inflammatory mediators, such as IL6 [10, 11].

Despite improvement in treatment strategies, trauma-hemorrhage patients may still develop severe inflammatory response that leads too MODS and finally death. Experimental treatment strategies aimed at neutralizing bioactive cytokines, such as monoclonal antibodies against TNF-α, have been successfully applied in several inflammatory disorders, including Crohn's disease and Rheumatoid Arthritis [29, 30]. However, clinical studies using monoclonal antibodies against TNF-α showed no clinical effect in trauma-patients [31]. It has been suggested that TNF-α neutralising antibodies causes the accumulation of a large pool of TNF-α/anti-TNF-α pool, which act as a slow release reservoir that may lead to increased constant active TNF-α [32]. Therefore, aiming at therapies that decrease the production of TNF-α and IL-6 may be more beneficial in limiting tissue damage and mortality rates in trauma-hemorrhage patients than neutralization of already produced cytokines.

In hemorrhagic shock, TNF-α is secreted within minutes after cellular stimulation, while production stops after three hours, and TNF-α plasma levels become almost undetectable [9]. We demonstrate that hCG-related regulatory oligopeptides (LQGV (SEQ ID NO:1), AQGV (SEQ ID NO:2), LAGV (SEQ ID NO:10)), administered 30 minutes after the induction of hemorrhagic shock, significantly reduced TNF-α and IL-6 plasma levels. Whether the effect on IL-6 production is direct, or indirect due to reduced TNF-α plasma levels cannot be concluded from our data. Nevertheless, establishing a reduction of IL-6 is of clinical importance, because high IL-6 plasma levels correlate with poor outcome and decreased survival in patients with severe trauma and infection [33, 34]. Cells within the liver, are considered as the main producers of pro-inflammatory cytokines during hemorrhagic shock [17]. TNF-α and IL-6 transcript levels were significantly increased in the livers of the HS group. LQGV (SEQ ID NO:1), AQGV (SEQ ID NO:2) or LAGV (SEQ ID NO:10) treatment was associated with a reduction in TNF-α and IL-6 liver transcripts, which may be indicative of decreased transcriptional activation. Another important characteristic of endothelial cells and hepatocytes during hemorrhagic shock is increased expression of the adhesion molecule ICAM-1 [7, 8]. Our study confirms the increased ICAM-1 expression in the liver after hemorrhagic shock. However, LQGV (SEQ ID NO:1), AQGV (SEQ ID NO:2), or LAGV (SEQ ID NO:10) treatment did not result in reduced ICAM-1 expression. This could be due to the inability of hCG-related oligopeptides to interfere with induction of ICAM-1 transcription. In lungs, ileum and sigmoid, we detected no effect of hemorrhagic shock on the induction of TNF-α, IL-6 and ICAM-1 transcripts. This confirms that the liver is the first organ in which the inflammatory response is initiated after hemorrhagic shock and fluid resuscitation [15, 31, 32]. In summary, a single administration of a synthetic hCG-related oligopeptide (LQGV (SEQ ID NO:1), AQGV (SEQ ID NO:2), LAGV (SEQ ID NO:10)) after the induction of severe trauma-hemorrhage reduces the subsequent pro-inflammatory response. These data suggest that these oligopeptides have therapeutic potential, in minimizing the late life threatening tissue- and organ-damage that is associated with SIRS seen with severe burns.

EXAMPLES

Treatment of Severe Skin Inflammations Such as Seen with Burns

To assess the activity of the various peptides with skin inflammations seen for example with burn patients an animal model was developed in which these inflammations are generated via topical application of an inflammatory agent to the skin of experimental mice. For this purpose mice were treated with 4% or 5% imiquimod. Imiquimod is an immune response modifier. It is manufactured as a 4 or 5% cream (ALDARA™). Imiquimod works by stimulating the immune system to release a number of chemicals called cytokines whereby it results in inflammation. The imiquimod is taken up by the so-called 'toll-like receptor 7' on certain immune cells that are found in the outside part of the skin, the epidermis. Skin areas treated with imiquimod will be come inflamed. The effects include itching, burning, redness, ulceration (sores), scabbing, flaking and pain. Particularly the mice treated with the 5% cream developed the intense inflammatory skin lesions often seen with burn wounds in burn patients.

Figure 11A:
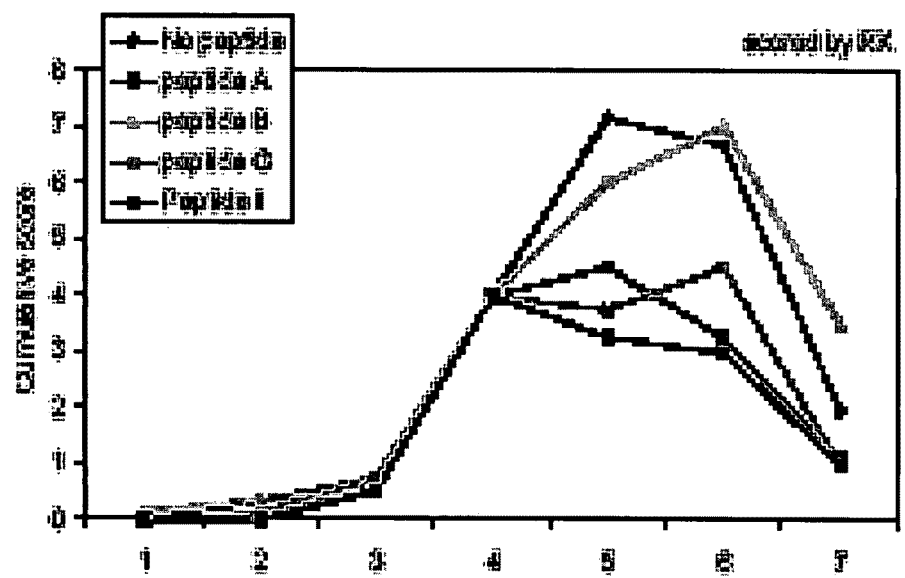
FIGS. 11A and 11B depict the same experiment but reflect the scores of two independent observers RK and JV. Peptide A=LAGV (SEQ ID NO:10); Peptide B=AQGV (SEQ ID NO:2); Peptide G=VLPALPQ (SEQ ID NO:13); Peptide I=LQGV (SEQ ID NO:1). Treatment protocol: Daily application of 4% imiquimod cream (day 0-day 6) on shaved back, 300 µg/mouse peptide in PBS i.p. on day −1, 1, 3 and 5, Scoring for redness, scaling and skin thickness, daily, blindly. Cumulative score=redness+scaling+thickness (scale 0-12).
Figure 11B:
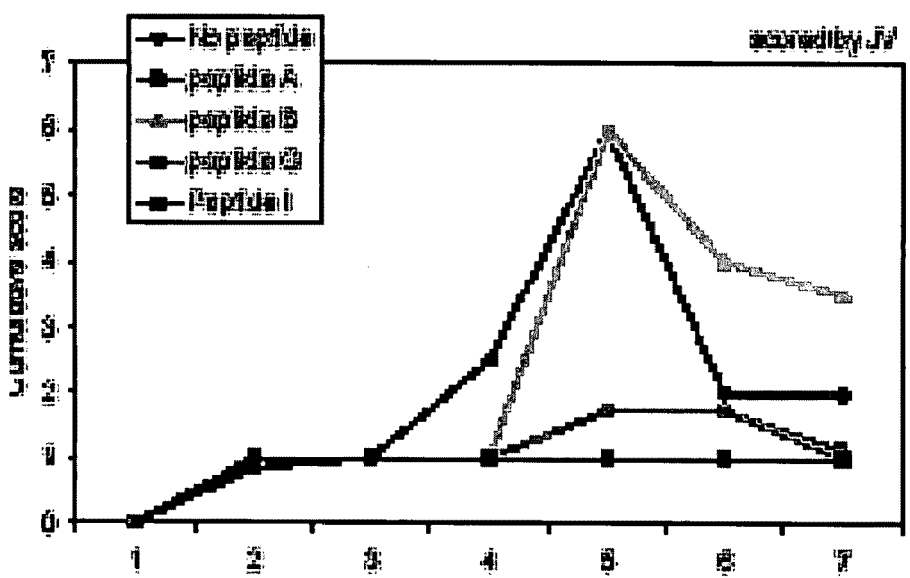
Figure 12:
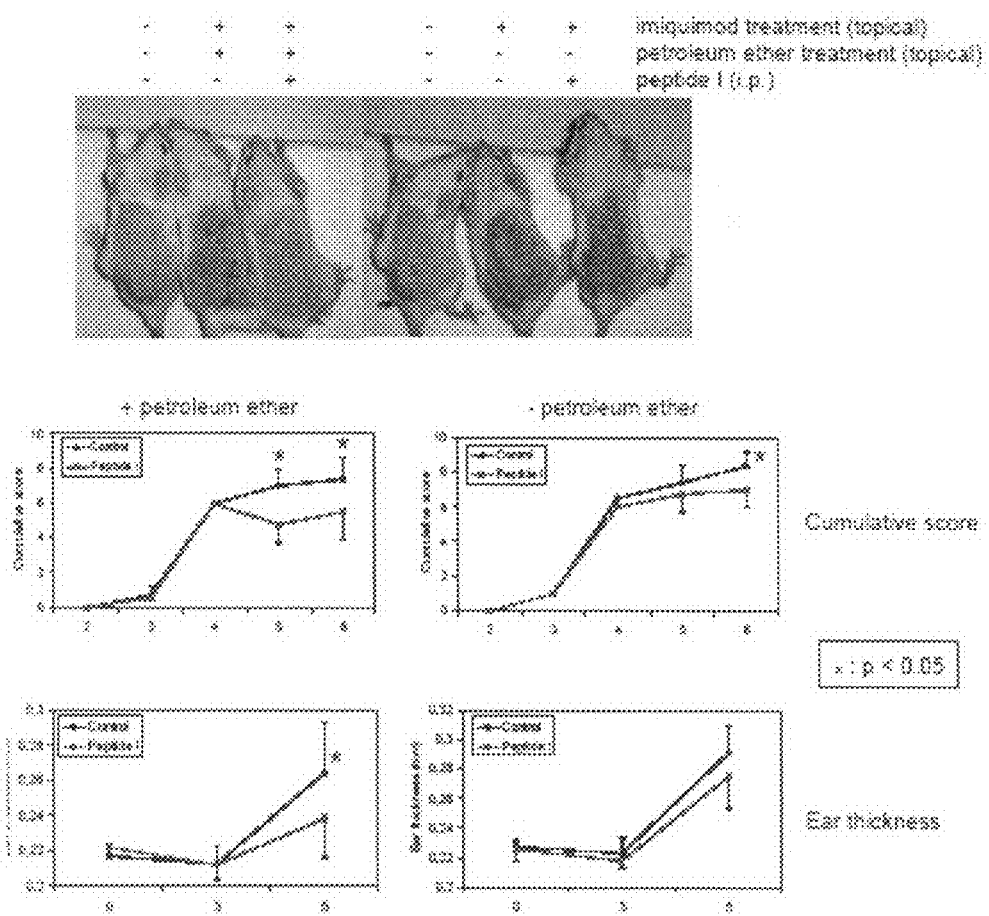
FIG. 12 Peptide I=LQGV (SEQ ID NO:1), Treatment protocol: Daily application of 5% imiquimod cream (day 1-day 5) on shaved back and ear. Immediately before imiquimod application, treat skin from back and ear with petroleum ether to remove fat and scales (also groups not treated with petroleum ether). 500 µg/mouse peptide I in PBS i.p. on day 1, 3 and 5. Measuring ear thickness on day 1, 3, and 5. Scoring for redness, scaling and skin thickness, daily, blindly. Cumulative score=redness+scaling+thickness (scale 0-12).

Peptides tested in this study were Peptide A (LAGV (SEQ ID NO:10)); Peptide B (AQGV (SEQ ID NO:2)); Peptide G (VLPALPQ (SEQ ID NO:13)) and Peptide I (LQGV (SEQ ID NO:1)). Peptides were given parenterally by intraperitoneal injection (i.p.). All peptides had beneficial activity on the imiquimod induced skin lesions, especially after the lesions had occurred (see FIGS. 11 and 12). Treatment with petroleum ether to remove fat and scales of the imiquimod induced lesions in one experiment improved the activity of peptide I (LQGV (SEQ ID NO:1))

REFERENCES

1. Vincent J L., Carlet, J., Opal, S. M., eds., *The sepsis text*, 2002
2. Cohen J. The immunopathogenesis of sepsis. *Nature* 2002; 420:885-891
3. Osborn T M, Tracy J K, Dunne J R, Pasquale M, Napolitano L M. Epidemiology of sepsis in patients with traumatic injury. *Crit. Care Med.* 2004; 32(11):2234-40
4. DS, Lefering R, Wade C E. Impact of hemorrhage on trauma outcome: an overview of epidemiology, clinical presentations, and therapeutic considerations. *J Trauma*, 2006, 60(6):S3-11.
5. Muylle L. The role of cytokines in blood transfusion reactions. *Blood Rev* 1995; 9:77-83.
6. Matsutani T, Kang S C, Miyashita M, Sasajima K, Choudhry M A, Bland K I, et al. Liver cytokine production and ICAM-1 expression following bone fracture, tissue trauma, and hemorrhage in middle-aged mice. *Am J Physiol Gastrointest Liver Physiol* 2007; 292:268-74
7. Rothoerl R D, Schebesch K M, Kubitza M, Woertgen C, Brawanski A, Pina A L. ICAM-1 and VCAM-1 expression following aneurysmal subarachnoid hemorrhage and their possible role in the pathophysiology of subsequent ischemic deficits. *Cerebrovasc Dis* 2006; 22:143-9
8. Sun L L, Ruff P, Austin B, Deb S, Martin B, Burris D, et al. Early up-regulation of intercellular adhesion molecule-1 and vascular cell adhesion molecule-1 expression in rats with hemorrhagic shock and resuscitation. *Shock* 1999; 11:416-22.
9. Ferguson K L, Taheri P, Rodriguez J, Tonapi V, Cardellio A, Dechert R. Tumor necrosis factor activity increases in the early response to trauma. *Acad Emerg Med.* 1997; 4(11): 1035-40.
10. Mainous M R, Ertel W, Chaudry I H, Deitch E A. The gut: a cytokine-generating organ in systemic inflammation? *Shock* 1995; 4:193-9
11. Yang R, Han X, Uchiyama T, Watkins S K, Yaguchi A, Delude R L, Fink M P, IL-6 is essential for development of gut barrier dysfunction after hemorrhagic shock and resuscitation in mice. *Am J Physiol Gastrointest Liver Physiol.* 2003; 285(3):G621-9
12. Taniguchi T, Koido Y, Aiboshi J, Yamashita T, Suzaki S, Kurokawa A, Change in the ratio of interleukin-6 to interleukin-10 predicts a poor outcome in patients with systemic inflammatory response syndrome. *Crit. Care Med* 27:1999; 1262-1264.

13. Snyder E L. The role of cytokines and adhesive molecules in febrile non-hemolytic transfusion reactions. *Immunol Invest* 1995; 24:333-9.
14. Winkelstein A, Kiss J E. Immunohematologic disorders. *Jama* 1997; 278:1982-92.
15. Davenport R. Cytokines and erythrocyte incompatibility. *Curr Opin Hematol* 1994; 1:452-6
16. Davenport R D. The role of cytokines in hemolytic transfusion reactions. *Immunol Invest* 1995; 24:319-31.
17. Zhu X L, Zellweger R, Zhu X H, Ayala A, Chaudry I H, Cytokine gene expression in splenic macrophages and Kupffer cells following haemorrhage, *Cytokine.* 1995; 7(1):8-14.
18. Fong Y, Tracey K J., Moldawer L L, Hesse D G, Manogue K B, Kenney J S., Lee A T, Kuo G C, Allison A C, Lowry S F, Cermani C A, Antibodies to cachectin/tumor necrosis factor reduce interleukin 1 beta and interleukin 6 appearance during lethal bacteremia, *J. Exp. Med.,* 1989; 1; 170 (5):1627-33
19. Robinson M K, Rounds J D, Hong R W, Jacobs D O, Wilmore D W. Glutathione deficiency increases organ dysfunction after hemorrhagic shock. *Surgery* 1992; 112:140-7; discussion 8-9
20. Sacks G, Sargent I, Redman C, An innate view of human pregnancy. Immunol Today, 1999, 20(3):114-8
21. Muyan M. and Boime I., Secretion of chorionic gondatrophin from human trophoblast. *Placenta,* 1997; 19(4): 237-41
22. Alexander H, Zimmermann G, Lehmann M, Pfeiffer R, Schone E, Leiblein S, Ziegert, M, HCG secretion by peripheral mononuclear cells during pregnancy, *Domest Anim Endocrinol.;* 1998; 15(5):377-87
23. Khan N A, Khan A, Savelkoul H F, Benner R, Inhibition of diabetes in NOD mice by human pregnancy factor. *Hum Immunol.,* 2001, 62(12):1315-23.
24. Cole L A, The deactivation of hCG by nicking and dissociation. *J. Clin Endocrinical metab.,* 1993; 76(3)704-10
25. Benner R, Khan N A. Dissection of systems, cell populations and molecules. *Scand J Immunol* 2005; 62 Suppl 1:62-6
26. Khan N A, Khan A, Savelkoul H F, Benner R. Inhibition of septic shock in mice by an oligopeptide from the beta-chain of human chorionic gonadotrophin hormone. *Hum Immunol* 2002; 63:1-7
27. Beillard E, Pallisgaard N, van der Velden V H, Bi W, Dee R, van der Schoot E, Delabesse E, Macintyre E, Gottardi E, Saglio G, Watzinger F, Lion T, van Dongen J J, Hokland P, Gabert J. Evaluation of candidate control genes for diagnosis and residual disease detection in leukemic patients using 'real-time' quantitative reverse-transcriptase polymerase chain reaction (RQ-PCR)—a Europe against cancer program. *Leukemia.* 2003; 17:2474-2486.
28. Childs E W, Wood J G, Smalley D M, Hunter F A, Cheung L Y. Leukocyte adherence and sequestration following hemorrhagic shock and total ischemia in rats. *Shock.* 1999; 11(4):248-52
29. Suenaert P, Bulteel V, Lemmens L, Noman M, Geypens B, Van Assche G, Geboes K, Ceuppens J L, Rutgeerts P. Anti-tumor necrosis factor treatment restores the gut barrier in Crohn's disease, *Am J. Gastroenterol.* 2002; 97(8): 2000-4.
30. Olsen N J, Stein C M. New drugs for rheumatoid arthritis. *N Engl J. Med.* 2004 350(21):2167-79
31. Kox W J, Volk T, Kox S N, Volk H D, Immunomodulatory therapies in sepsis. *Intensive Care Med.,* 2000, 26 (1)5124-8
32. Jit M, Henderson B, Stevens M, Seymour R M, TNF-alpha neutralization in cytokine-driven diseases: a mathematical model to account for therapeutic success in rheumatoid arthritis but therapeutic failure in systemic inflammatory response syndrome. *Rheumatology,* 2005 March; 44(3):323-31.
33. Yang R, Han X, Uchiyama T, Watkins S K, Yaguchi A, Delude R L, Fink M P, IL-6 is essential for development of gut barrier dysfunction after hemorrhagic shock and resuscitation in mice. *Am J Physiol Gastrointest Liver Physiol.* 2003; 285(3):G621-9
34. Taniguchi T, Koido Y, Aiboshi J, Yamashita T, Suzaki S, Kurokawa A, Change in the ratio of interleukin-6 to interleukin-10 predicts a poor outcome in patients with systemic inflammatory response syndrome. *Crit. Care Med* 27:1999; 1262-1264
35. Stites D P, Pavia C S, Clemens L E, Kuhn R W, Siiteri P K, Immunologic regulation in pregnancy, *Arthritis Rheum.* 1979 22(11):1300-7.
36. Saito S, Cytokine network at the feto-maternal interface, *J Reprod Immunol.,* 2000, 47(2):87-103.
37. Puett D, Li Y, DeMars G, Angelova K, Fanelli F, A functional transmembrane complex: the luteinizing hormone receptor with bound ligand and G protein, *Mol Cell Endocrinol.* 2007 2; 260-262:126-36.
38. Bai J P F, Subramanian P, Mosberg H I and Amidon G L, Structural requirements for the intestinal mucosal-cell peptide transport: the need for N-terminal α-amino group, 1991, *Pharm Res* 8: 593-599.
39. Yang R, Tan X, Thomas A M, Steppacher R, Qureshi N, Morrison D C, Van Way C W 3rd. Alanine-glutamine dipeptide (AGD) inhibits expression of inflammation-related genes in hemorrhagic shock. *J Parenter Enteral Nutr.* 2007; 31(1):32-6.

What is claimed is:

1. A method for modulating a burn injury in a subject, the method comprising:
providing the subject with a gene-regulatory peptide selected from the group consisting of LQG, AQG, LQGV (SEQ ID NO:1), AQGV (SEQ ID NO:2), LQGA (SEQ ID NO:3), VLPALP (SEQ ID NO:4), ALPALP (SEQ ID NO:5), VAPALP (SEQ ID NO:6), ALPALPQ (SEQ ID NO:7), VLPAAPQ (SEQ ID NO:8), VLPALAQ (SEQ ID NO:9), LAGV (SEQ ID NO:10), VLAALP (SEQ ID NO:11), VLPALA (SEQ ID NO:12), VLPALPQ (SEQ ID NO:13), VLAALPQ (SEQ ID NO:14), VLPALPA (SEQ ID NO:15), GVLPALP (SEQ ID NO:16), LPGC (SEQ ID NO:19), MTRV (SEQ ID NO:20), MTR, and VVC.

2. The method according to claim 1 wherein the gene-regulatory peptide is selected from the group consisting of LAGV (SEQ ID NO:10), AQGV (SEQ ID NO:2), VLPALPQ (SEQ ID NO:13), and LQGV (SEQ ID NO:1).

3. The method according to claim 2 wherein the gene-regulatory peptide is selected from the group consisting of LAGV (SEQ ID NO:10), AQGV (SEQ ID NO:2), and LQGV (SEQ ID NO:1).

4. The method according to claim 1, wherein the subject is at risk of experiencing a systemic inflammatory response syndrome occurring after the burn injury.

5. The method according to claim 1, further comprising providing the subject with an agent directed against disseminated intravascular coagulation.

6. The method according to claim 5 wherein the agent has Activated Protein C activity.

7. The method according to claim 1, further comprising providing the subject with a bacteristatic compound comprising silver.

8. The method according to claim 1 wherein providing the subject with a gene-regulatory peptide inhibits the activity of a NF-kappaB/Rel protein.

* * * * *